(12) United States Patent
Lopansri et al.

(10) Patent No.: US 11,090,447 B2
(45) Date of Patent: Aug. 17, 2021

(54) TAMPER-RESISTANT ENCLOSURES FOR FLUID LINES

(71) Applicant: Intermountain Intellectual Asset Management, LLC, Salt Lake City, UT (US)

(72) Inventors: Bert Kamolsit Lopansri, Park City, UT (US); Troy J. Orr, Draper, UT (US)

(73) Assignee: Intermountain Intellectual Asset Management, LLC, Salt Lake City, UT (US)

(*) Notice: Subject to any disclaimer, the term of this patent is extended or adjusted under 35 U.S.C. 154(b) by 156 days.

(21) Appl. No.: 16/352,414

(22) Filed: Mar. 13, 2019

(65) Prior Publication Data

US 2019/0275263 A1 Sep. 12, 2019

Related U.S. Application Data

(63) Continuation of application No. 15/380,984, filed on Dec. 15, 2016, now abandoned.
(Continued)

(51) Int. Cl.
*A61M 5/50* (2006.01)
*A61M 39/02* (2006.01)
(Continued)

(52) U.S. Cl.
CPC .......... *A61M 5/5086* (2013.01); *A61M 5/002* (2013.01); *A61M 39/02* (2013.01);
(Continued)

(58) Field of Classification Search
CPC .... A61M 5/5086; A61M 5/002; A61M 39/08; A61M 5/10; A61M 5/1011; A61M 5/16;
(Continued)

(56) References Cited

U.S. PATENT DOCUMENTS 4,194,509 A * 3/1980 Pickering ........... A61M 39/1011
604/111
4,286,640 A * 9/1981 Knox .................... A61J 1/1406
215/249

(Continued)

OTHER PUBLICATIONS

Lopansri, et al., Office Action dated Oct. 18, 2018 for U.S. Appl. No. 15/380,984.

*Primary Examiner* — Bhisma Mehta
*Assistant Examiner* — James D Ponton
(74) *Attorney, Agent, or Firm* — Stoel Rives LLP; Jordan B. Olsen

(57) ABSTRACT

A tamper-resistant device for holding a portion of an access port of a fluid line can include a first housing member that includes a first recess and a first stopping shelf. The device can further include a second housing member that includes a second recess and a second stopping shelf. The second housing member can couple with the first housing member such that the first and second stopping shelves cooperate to retain the portion of the access port within the device. The device can include a locking mechanism configured maintain the first and second housing members in a coupled state when engaged. The device can further include a tamper-evident indicator that, when activated, permits the first and second housing members to transition from the coupled state to a decoupled state to permit access to the access port of the fluid line.

16 Claims, 22 Drawing Sheets

Related U.S. Application Data

(60) Provisional application No. 62/267,902, filed on Dec. 15, 2015.

(51) Int. Cl.
  *A61M 39/10* (2006.01)
  *A61M 5/00* (2006.01)
  *A61M 39/08* (2006.01)

(52) U.S. Cl.
  CPC ............... *A61M 2039/087* (2013.01); *A61M 2039/1066* (2013.01)

(58) Field of Classification Search
  CPC ........ A61M 5/162; A61M 5/165; A61M 5/20; A61M 5/02; A61M 2039/087; A61M 2039/1005; A61M 2039/205; A61M 2039/1066; Y10S 604/905
  See application file for complete search history.

(56) References Cited

U.S. PATENT DOCUMENTS

| | | |
|---|---|---|
| 4,517,971 A | 5/1985 | Sorbonne |
| 4,624,664 A * | 11/1986 | Peluso ................ A61M 39/165 604/256 |
| 5,116,324 A | 5/1992 | Brierley et al. |
| 5,385,373 A * | 1/1995 | Love .................... F16B 41/007 24/16 PB |
| 5,531,695 A | 7/1996 | Swisher |
| 6,283,945 B1 | 9/2001 | Bierman |
| D609,338 S | 2/2010 | Dozier, Jr. |
| 7,678,101 B2 | 3/2010 | Sage |
| 7,967,792 B2 | 6/2011 | Bierman |
| 8,251,956 B2 | 8/2012 | Bierman et al. |
| 8,419,689 B2 | 4/2013 | Fink et al. |
| 8,474,784 B2 | 7/2013 | Kashmirian et al. |
| 8,556,859 B2 | 10/2013 | Nilson et al. |
| 8,603,022 B2 | 12/2013 | Lyons et al. |
| 8,715,242 B2 | 5/2014 | Helm, Jr. |
| 8,771,231 B2 | 7/2014 | Makino et al. |
| 8,858,505 B1 | 10/2014 | Justus et al. |
| 2001/0011164 A1 | 8/2001 | Bierman |
| 2002/0165494 A1 | 11/2002 | Bierman |
| 2006/0178627 A1 | 8/2006 | Geiger et al. |
| 2006/0247577 A1 | 11/2006 | Wright |
| 2007/0055205 A1 | 3/2007 | Wright et al. |
| 2008/0054632 A1 | 3/2008 | Funamura et al. |
| 2009/0024090 A2 | 1/2009 | Wright et al. |
| 2009/0093769 A1 | 4/2009 | Wright et al. |
| 2010/0100049 A1 | 4/2010 | Godfrey |
| 2011/0118670 A1 | 5/2011 | Kay et al. |
| 2012/0197202 A1 | 8/2012 | Wright et al. |
| 2012/0232497 A1 | 9/2012 | Singh |
| 2014/0100533 A1 * | 4/2014 | Lyons ................... A61M 39/20 604/264 |
| 2014/0188078 A1 | 7/2014 | Peters |
| 2014/0303595 A1 * | 10/2014 | Justus ................. A61M 5/5086 604/508 |
| 2017/0165437 A1 | 6/2017 | Lopransi et al. |

* cited by examiner

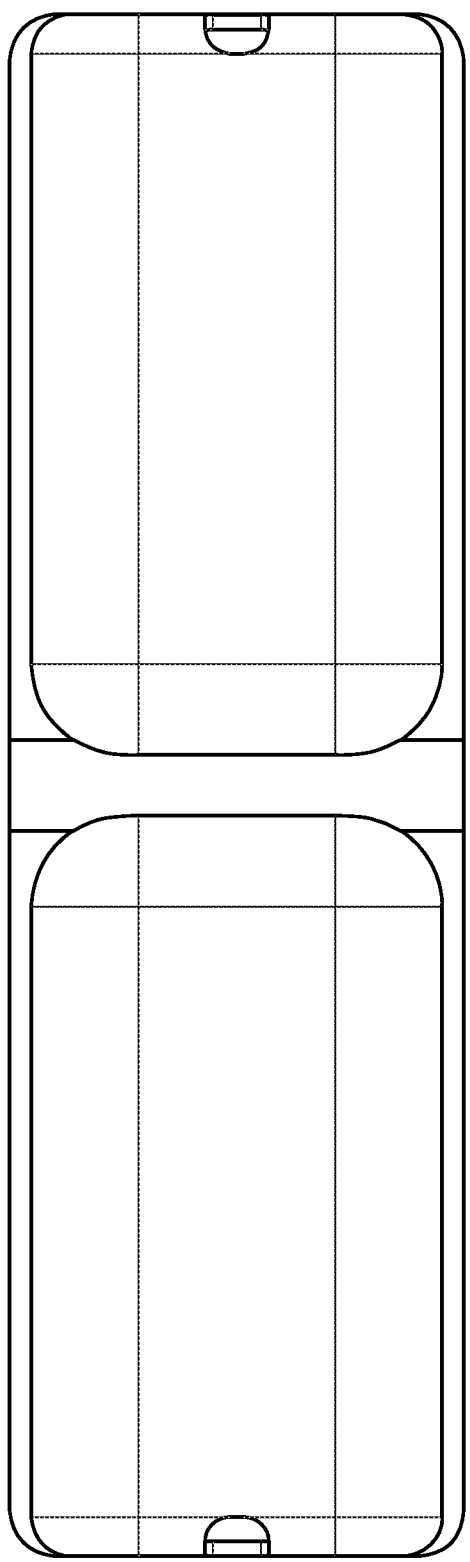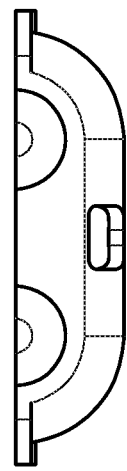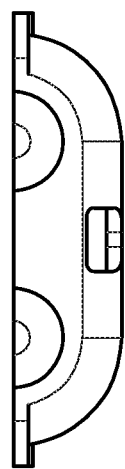
FIG. 13
FIG. 15
FIG. 14

TAMPER-RESISTANT ENCLOSURES FOR FLUID LINES

CROSS-REFERENCE TO RELATED APPLICATIONS

This application is a continuation of U.S. patent application Ser. No. 15/380,984, titled TAMPER-RESISTANT ENCLOSURES FOR FLUID LINES, filed on Dec. 15, 2016, which claims the benefit under 35 U.S.C. § 119(e) of U.S. Provisional Patent Application No. 62/267,902, titled TAMPER-RESISTANT CATHETER ENCLOSURES, filed on Dec. 15, 2015, the entire contents of each of which are hereby incorporated by reference herein.

BACKGROUND

The present disclosure relates to medical fluid lines and accessories thereof. In particular, the present disclosure relates to tamper-resistant enclosures for access portions of medical fluid lines.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 13 is a bottom plan view of the housing showing the exterior;

FIG. 14 is an end elevation view of the housing;

FIG. 15 is an opposite end elevation view of the housing;

DETAILED DESCRIPTION

In various circumstances, it can be desirable to prevent tampering with an access end of a medical fluid line. For example, in some instances it can be desirable to prevent a patient from accessing an IV line or other catheter system that is in fluid communication with the patient, such as for dispensing injectable narcotics or other drugs to the patient (e.g., for purposes of abusing the narcotics). In some instances, the patient may have a peripherally inserted central catheter (PICC) line, and may be treated on an outpatient basis. It can be desirable to ensure that the patient does not self-medicate or otherwise abuse drugs between visits to the hospital or between home visits from medical professionals. A tamper-resistant and/or tamper-evident enclosure about the access end of the PICC line can help prevent such unauthorized access and/or detect the unauthorized access after it has occurred. In other or further instances, it can be desirable to ensure that a sterility cap that is placed on the access end of the medical fluid line remains in place. These and/or other advantages can be achieved via embodiments disclosed herein, as will be appreciated from the drawings and description that follows.

As used herein, the term "tamper-resistant" encompasses both the ability to physically resist tampering, as well as resist tampering due, at least in part, to a deterrent effect. For example, a tamper-resistant feature may be present where the feature provides little to no physical barrier to tampering, yet readily demonstrates (e.g., visibly indicates) that tampering has occurred. Such a feature is considered "tamper-resistant," in that it resists the tampering by dissuading or otherwise providing disincentives to tampering.

Figure 1:
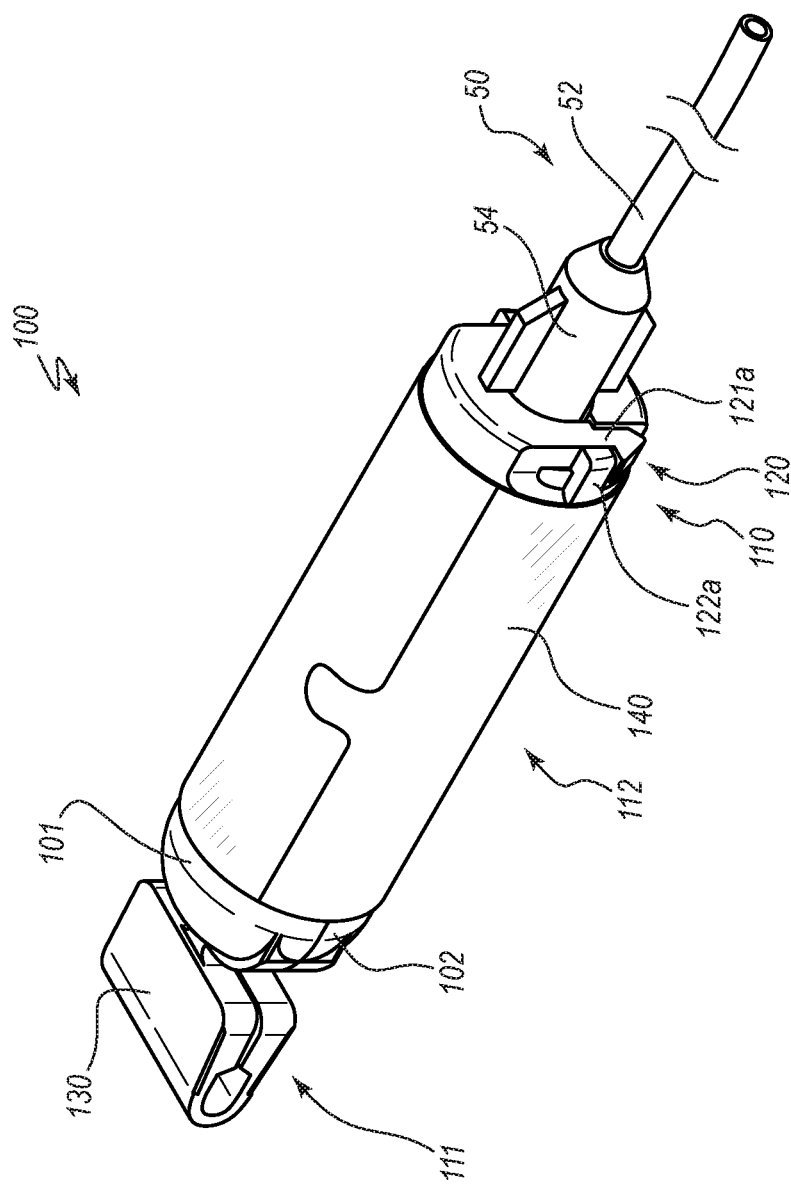
FIG. 1 is a perspective view of an embodiment of a tamper-resistant enclosure in a closed state and encompassing a proximal end of a medical fluid line to prevent undetected access thereto.

FIG. 1 depicts an embodiment of a tamper-resistant enclosure 100, which may also be referred to as a tamper-resistant apparatus or tamper-resistant device. The tamper-resistant enclosure 100 includes a first housing member 101 and a second housing member 102. In the illustrated embodiment, the first and second housing members 101, 102 are in a closed state or configuration and enclose within an interior thereof a proximal end of a medical fluid line 50. The terms "enclose" and "enclosure" do not necessarily imply an ability or necessity to enclose completely. For example, although in the illustrated embodiment, the first and second housing members 101, 102 of the tamper-resistant enclosure 100 fully encompass the proximal end of the medical fluid line 50, such that the proximal end is obscured, hidden from view, or otherwise inaccessible from all angles, other arrangements are possible. For example, in some embodiments, one or more windows or other openings may be present, yet the tamper-resistant device may sufficiently encompass the proximal end of the medical fluid line 50 to prevent access to the fluid line.

The medical fluid line 50 can be of any suitable variety, such as an IV line or a catheter line. For example, the fluid line 50 may include a PICC catheter that includes a medical connector 54 at a proximal end thereof, with a distal end of the catheter positioned within a patient. In the illustrated embodiment, the fluid line 50 includes a catheter 52 with a medical connector 54 attached to a proximal end thereof. The medical connector 54 may be of any suitable variety. In the illustrated embodiment (as discussed further below), the connector 54 is a luer connector.

The illustrated embodiment includes three tamper-evident indicators 110, 111, 112. The tamper-evident indicator 110 comprises a pair of irreversible locks 120 (only one lock 120 is visible in FIG. 1), the tamper-evident indicator 111 comprises a removable hinge 130, and the temper-evident indicator 112 comprises a tamper-evident sticker 140.

More or fewer tamper-evident indicators are possible. In the illustrated embodiment, each tamper-evident indicator 110, 111, 112 is in an undisrupted state when the tamper-resistant enclosure 100 is in the closed configuration depicted in FIG. 1. Further, each tamper-evident indicator 110, 111, 112 can physically assist in maintaining the enclosure 100 in the closed state.

In the illustrated embodiment, when actuated, or moved to a release state, each tamper-evident indicator 110, 111, 112 can permit the first and second housing members 101, 102 to transition from the coupled state, as depicted, to a decoupled state to permit access to the proximal end of the medical fluid line 50. In some instances, one or more of the tamper-evident indicators 110, 111, 112 must be actuated, or moved to the release state, in order to decouple the first and second housing members 101, 102 from each other. As discussed further below, in the illustrated embodiment, it is not possible to separate the first and second housing members 101, 102 from each other unless the tamper-evident indicator 112 is actuated (e.g., the sticker 140 is removed or otherwise altered to permit separation of the first and second housing members 101, 102). In contrast, once the tamper-evident indicator 112 has been removed, the first and second housing members 101, 102 can be separated from each other by either actuating the tamper-evident indicator 110, the tamper-evident indicator 111, or both of the tamper-evident indicators 110, 111.

In the illustrated embodiment, the depicted irreversible lock 120 includes a pair of interlocking arms 121a, 122a. Operation of the arms 121a, 122a is described further below. For example, in some embodiments, one or more of the arms 121a, 122a is configured to deform, break, or otherwise indicate that tampering has occurred when the lock 120 are transitioned from the locking mode depicted in FIG. 1 to an unlocked mode.

In other embodiments, the locks 120 may be selectively opened after having been closed, or may not have the ability to demonstrate that they have been opened after having been in a locking state. Stated otherwise, the locks 120 may not have the capacity to demonstrate that tampering has occurred—for example, neither of the arms 121a, 122a may demonstrate deformation, damage, separation, or other tampering evidence when moved out of the locking mode. In such instances, the tamper-evident indicator 110 is omitted. Rather, the locks 120 merely serve the function of maintaining the first and second housing members 101, 102 in the coupled state.

Operations of the removable hinge 130 of the tamper-evident indicator 111 and the sticker 140 of the tamper-evident indicator 112 are discussed further below.

Figure 2A:
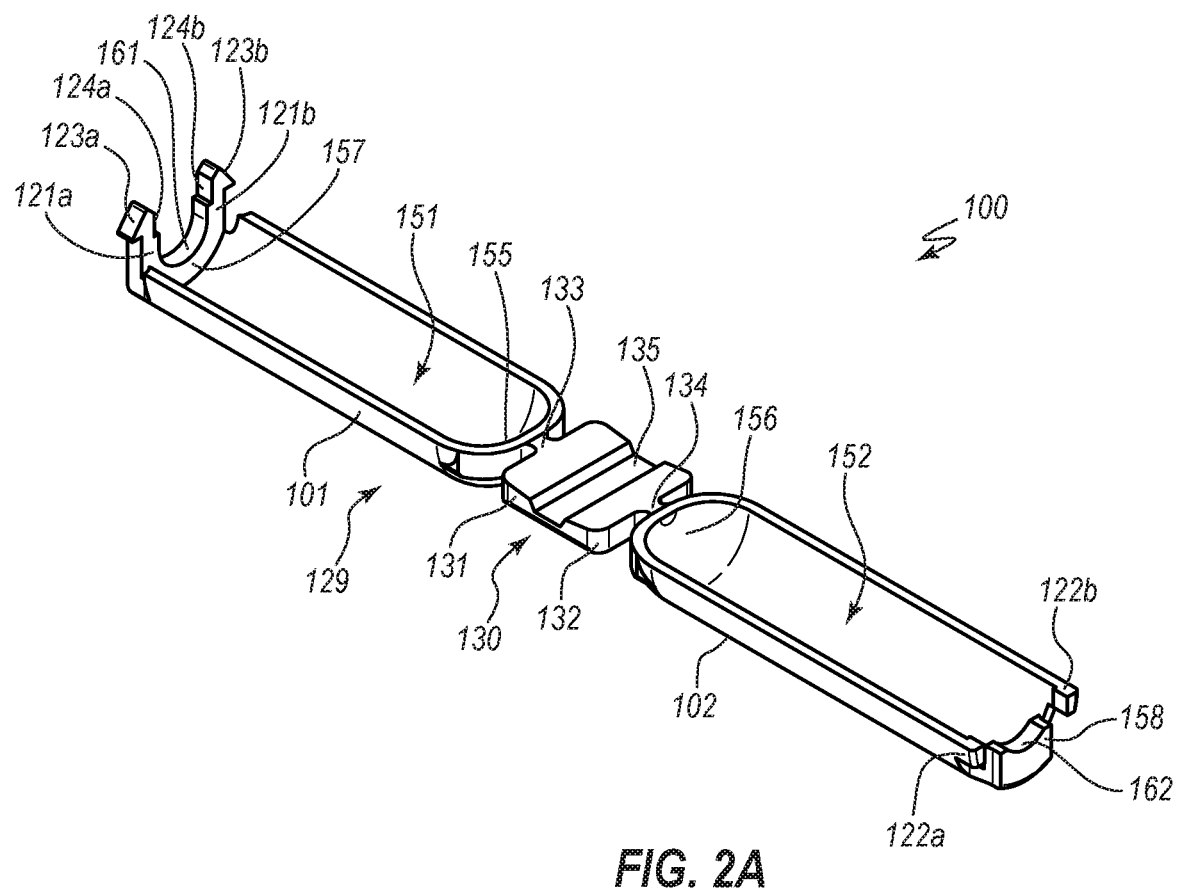
FIG. 2A is a perspective view of the tamper-resistant enclosure in an open state, and represents an early stage in an illustrative method of using the tamper-resistant enclosure.

FIGS. 2A-2I depict various stages of an illustrative method of using the tamper-resistant enclosure 100. FIG. 2A is a perspective view of the tamper-resistant enclosure 100 in an open state that represents an early stage of the illustrative method.

Figure 2B:
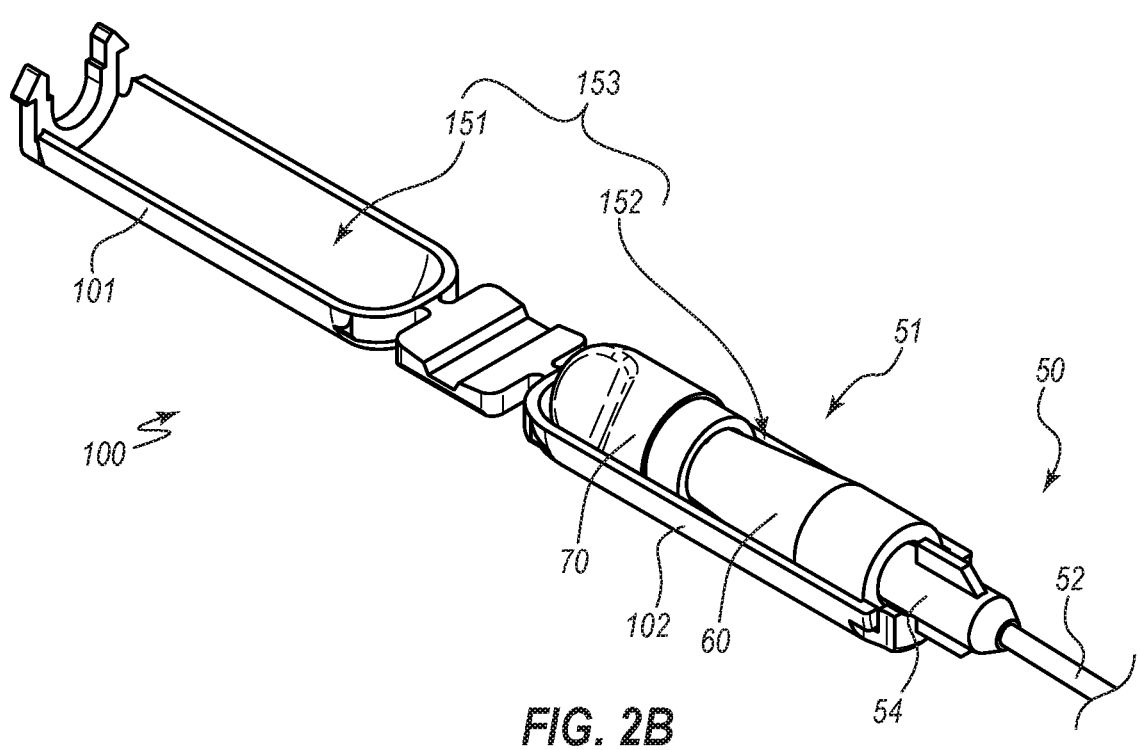
FIG. 2B is a perspective view of the tamper-resistant enclosure in the open state of FIG. 2A with a proximal end of a medical fluid line positioned within a recess of one of the housing members of the tamper-resistant enclosure, and represents a subsequent stage of the illustrative method.

The first housing member 101 defines a recess 151, and the second housing member 102 defines a second recess 152. As shown in FIGS. 2B and 4, when the housing members 101, 102 are in the coupled state, the first and second recesses 151, 152 cooperate do define a cavity into which the proximal end of the medical fluid line 50 is received. In the illustrated embodiment, each of the first and second housing members is substantially pill shaped. Stated otherwise, the housing members 101, 102 are elongated in a longitudinal direction and include a rounded end. A central body portion of each housing member 101, 102 is substantially cylindrical.

Figure 5:
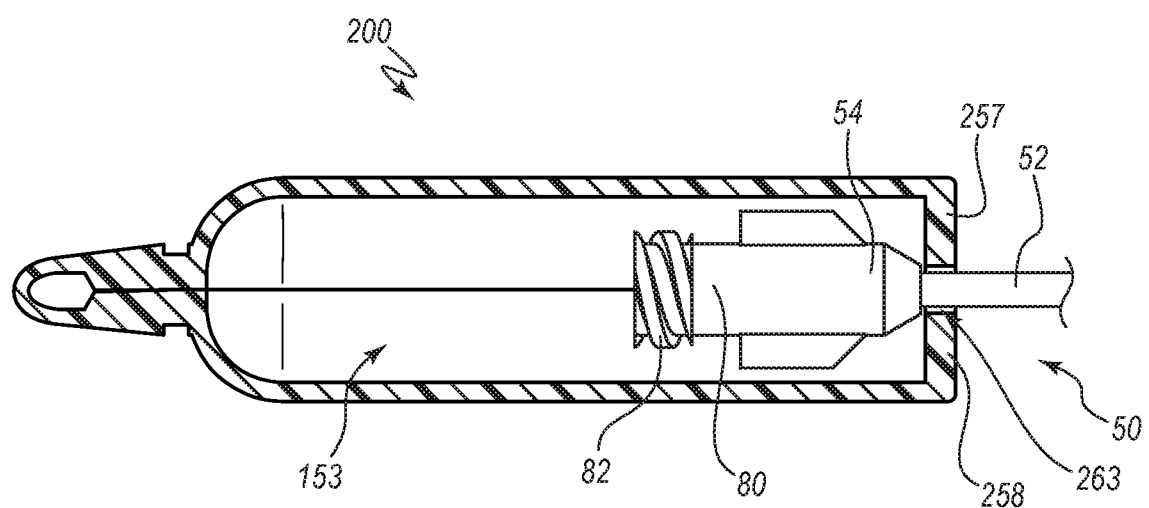
FIG. 5 is a cross-sectional view of another embodiment of a tamper-resistant enclosure in a closed state and encompassing a full connector portion at a proximal end of a medical fluid line.

In the illustrated embodiment, the first housing member 101 includes a closed end 155. Opposite the closed end 155, the first housing member 101 defines a first stopping shelf 157. Similarly, the second housing member 102 includes a closed end 156. Opposite the closed end 156, the second housing member 102 defines a second stopping shelf 158. Each stopping shelf 157, 158 defines a rounded opening surface 161, 162, respectively. As shown in FIG. 5, the opening surfaces 161, 162 can cooperate to define an opening 163 through which a portion of the medical fluid line 50 can extend when the enclosure 100 is in the closed state.

With continued reference to FIG. 2A, the hinge 130 can include a first hinge member 131 attached to the first housing member 101 via a first frangible section or frangible connection 133. The hinge 130 can likewise include a second hinge member 132 attached to the second housing member 102 via a second frangible section or frangible connection 134. In the illustrated embodiment, each frangible connection 133, 134 is defined as a narrow neck of material that can easily snap, break, or otherwise permit disconnection of the hinge members 131, 132 from the housing members 101, 102 when the hinge 130 is twisted, bent (e.g., repeatedly bent back and forth), or otherwise ruptured. Any other suitable breakable or frangible connection is contemplated. Stated otherwise, the hinge 130 is connected to the housing members 101, 102 via breakaway mechanisms. Any suitable breakaway mechanisms are contemplated.

The hinge 130 can further include a hinging region 135 at which bending is facilitated. In the illustrated embodiment, the hinging region 135 is a region of reduced material thickness. For example, the hinging region 135 may be a living hinge.

The first housing member 101 can define the locking arm 121a, as well as a locking arm 121b. In the illustrated embodiment, each locking arm 121a, 121b defines a camming surface 123a, 123b and a recessed surface 124a, 124b, respectively. Further, the second housing member 102 defines the locking arms 122a, 122b. These features are described further with respect to FIGS. 3A and 3B.

In the illustrated embodiment, the housing members 101, 102 and the hinge 130 are integrally formed from a unitary piece of material. Any suitable material may be used, and may desirably exhibit sufficient rigidity to protect the proximal end of the medical fluid line 50 when such is located therein, yet may exhibit flexibility or even resilience in other regions, such as regions of reduced thickness. For example, the material may readily bend at the hinging region 135 and/or may define locking arms 122a, 122b that are resiliently deformable. In various embodiments, the material can comprise, for example, plastic, including, without limitation, polypropylene (PP), polyethylene (PE), acetal, polyvinylchloride, silicone, or acrylonitrile butadiene styrene. In other embodiments, one or more components may be formed of one or more different or further materials.

FIG. 2B is a perspective view of the tamper-resistant enclosure 100 in the open state with a proximal end 51 of the medical fluid line 50 positioned within the recess 152 of the second housing member 102. In this example, the luer connector 54 is coupled with a needleless medical connector 60 of any suitable variety, which is in turn connected to a sterilizing or disinfecting cap 70 of any suitable variety. Accordingly, the cavity 153 defined by the first and second housing members 101, 102 is sufficiently large to accommodate multiple connected components at the proximal end 51 of the medical fluid line 50.

In the illustrated arrangement, the needleless medical connector 60 is the access port of the medical fluid line 50, as fluid may be introduced into or withdrawn from the line 50 thereat. In other instances, the needleless medical connector 60 may be omitted, and the luer connector 54 may instead be the access port of the medical fluid line 50. Any suitable access port configuration is contemplated.

The tamper-resistant enclosure 100 can prevent unauthorized access of the medical fluid line 50 via the access port (e.g., the connector 50 or the needleless connector 60). In further instances, such as the illustrated arrangement, the tamper-resistant enclosure 100 can ensure that the sterilization or disinfection cap 70 remains in sterilizing or disinfecting contact with the access port.

Figure 2C:
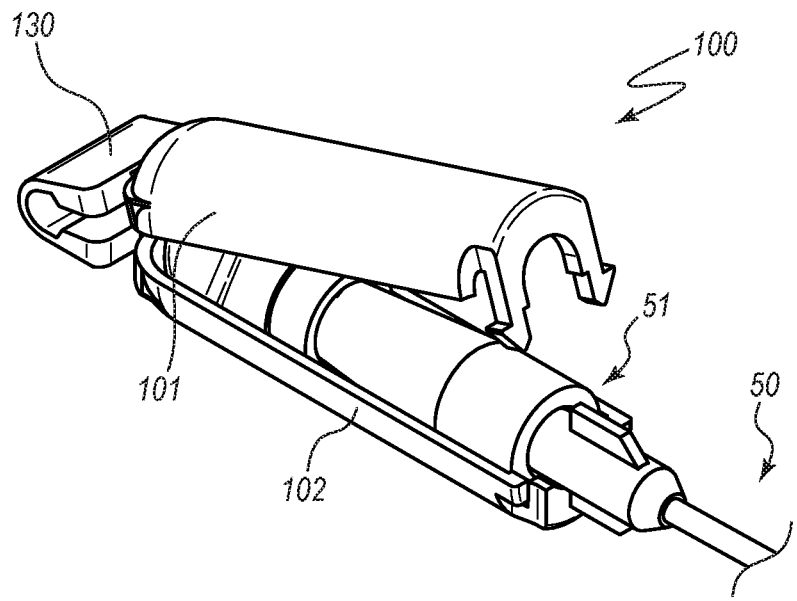
FIG. 2C is a perspective view of the tamper-resistant enclosure being transitioned from the open state to a closed state, and represents a stage of the illustrative method that is subsequent to that depicted in FIG. 2B.

FIG. 2C is a perspective view of the tamper-resistant enclosure being transitioned from the open state to the closed state. The first and second housing members 101, 102 and the hinge 130 may be referred to as a clamshell configuration.

Figure 2D:
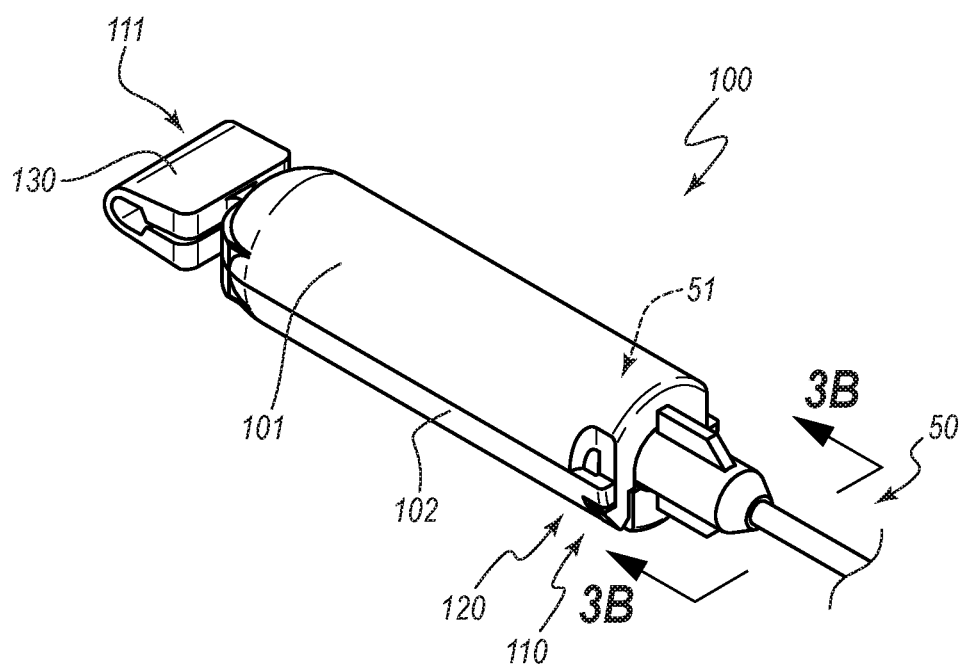
FIG. 2D is a perspective view of the tamper-resistant enclosure in the closed state encompassing the proximal end of the medical fluid line and preventing undetected access thereto, and represents a stage of the illustrative method that is subsequent to that depicted in FIG. 2C.

FIG. 2D is a perspective view of the tamper-resistant enclosure 100 in the closed state encompassing the proximal end 51 of the medical fluid line 50 and preventing undetected access thereto. In the illustrated stage of operation, the tamper-evident indicators 110 and 111 serve to ensure that the first and second housing members 101, 102 cannot be separated without leaving a trace that tampering has occurred. In particular, the irreversible lock 120 cannot be opened at the distal end of the enclosure 100 without being damaged or deformed in some manner (as discussed below). Likewise, the hinge 130 cannot be opened to permit access from the proximal end of the enclosure 100, but instead must first be removed to permit the access, which would provide evidence of tampering.

In some embodiments, only the tamper-evident indicators 110, 111 are used with the tamper-resistant enclosure 100. Accordingly, in such embodiments, FIG. 2D represents a fully assembled, fully closed device. However, in other embodiments, the additional tamper-evident indicator 112, such as the tamper-evident sticker 140, may also be used, as depicted in the optional stages of FIGS. 2E and 2F. The tamper-evident sticker 140 can provide a further level of tamper resistance, whether that tamper resistance is physical and/or dissuading in nature.

Figure 2E:
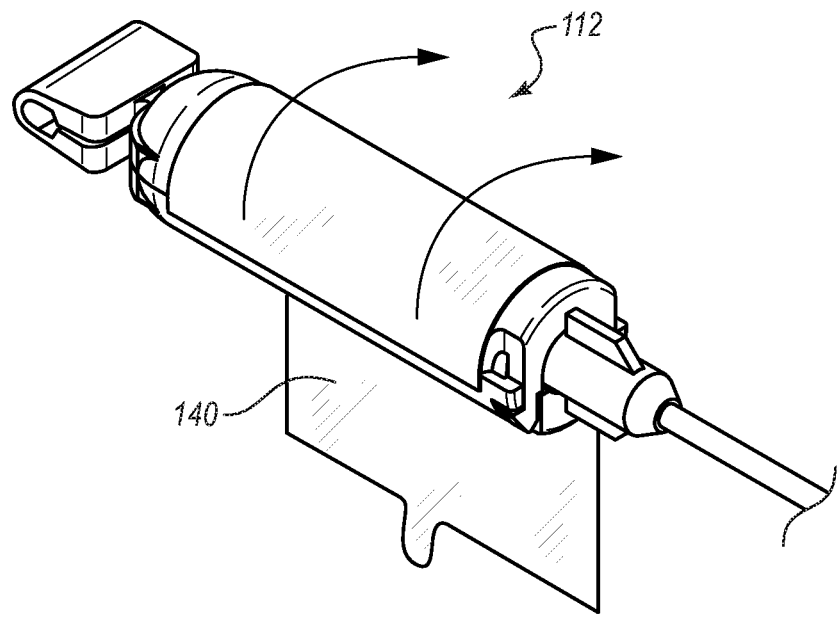
FIG. 2E is a perspective view of an early stage of application of a tamper-evident sticker to the tamper-resistant enclosure in the closed state, and represents a stage of an optional portion of the illustrative method that is subsequent to that depicted in FIG. 2D.

FIG. 2E is a perspective view of an early stage of application of the tamper-evident sticker 140 to the tamper-resistant enclosure 100 in the closed state. Any suitable variety of tamper-evident sticker 140 is contemplated, including, without limitation, such as stickers used for tamper evident sterile seals manufactured by Steri-Tamp® of Woodmere, N.Y. The tamper-evident sticker 140 can contact both the first and second housing members 101, 102 and assist in physically maintaining them in the coupled orientation.

Figure 2F:
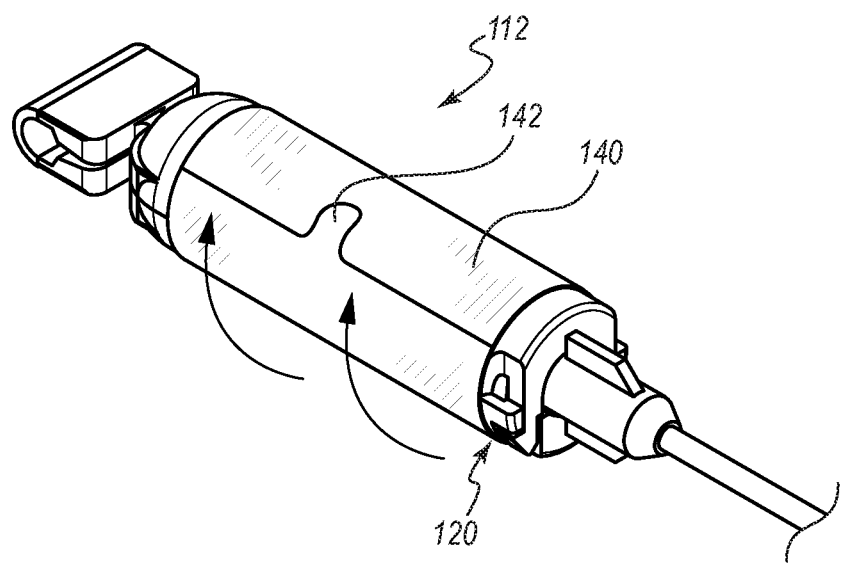
FIG. 2F is a perspective view of a late stage of application of the tamper-evident sticker to the tamper-resistant enclosure in the closed state, and represents a stage of the illustrative method that is subsequent to that depicted in FIG. 2E.

FIG. 2F is a perspective view of a late stage of application of the tamper-evident sticker 140 to the tamper-resistant enclosure 100 in the closed state. In the illustrated embodiment, the sticker 140 has been applied in a manner that leaves the lock 120 exposed. In other instances, the sticker 140 may be applied at a more distal position so as to cover the lock 120 and provide a further level of tamper-evidence, should someone attempt to open the enclosure 100 via the lock 120. The tamper-resistant sticker 140 can include a tab 142 to facilitate removal of the sticker.

In some embodiments, access to the proximal end 51 of the medical fluid line 50, such as by an authorized medical professional, may again be achieved by opening the device 100. In certain methods for achieving access, the tamper-resistant sticker 140 may first be removed, such as by pulling the tab 142 and pulling the sticker in the direction opposite the arrows in FIGS. 2E and 2F. As previously mentioned, such removal of the sticker 140 may be referred to as actuation or activation of the tamper-evident indicator 112. Of course, in some instances, the sticker 140 may indicate tampering when it is only partially removed, and not fully removed from both the housing members 101, 102. For example, such partial removal may evidence an aborted attempt to gain access to the proximal end 51 of the medical fluid line 50.

Figure 2G:
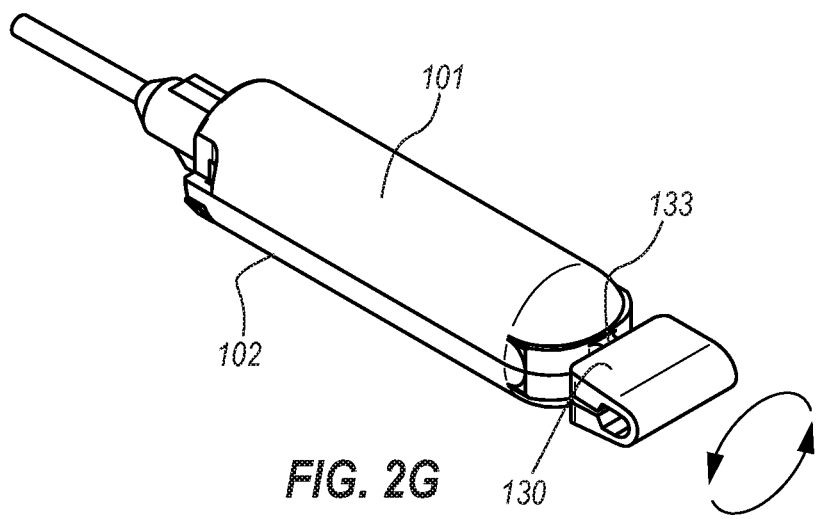
FIG. 2G is a perspective view of the tamper-resistant enclosure in the closed state—in some instances, after removal of the tamper-evident sticker—and depicting rotation of an embodiment of a hinge at a proximal end thereof, and represents a stage of the illustrative method that is subsequent to that depicted in either FIG. 2D or FIG. 2F.

FIG. 2G is a perspective view of the tamper-resistant enclosure 100 in the closed state after removal of the tamper-evident sticker 140. Quick access to the proximal end 51 of the medical fluid line 50 may be achieved by removing the hinge 130. In the illustrated method, the hinge 130 is removed by rotating it to break the frangible connections 133, 134. Rotation of the hinge 130 is depicted by curved arrows.

Figure 2H:
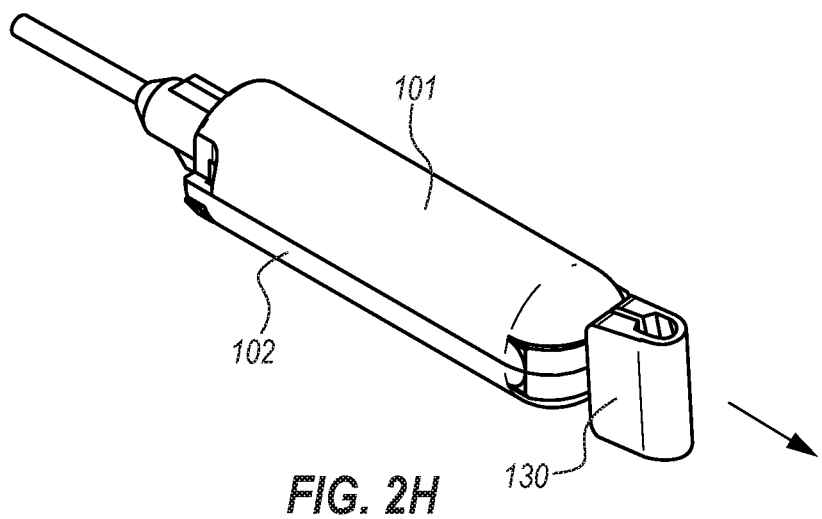
FIG. 2H is a perspective view of the tamper-resistant enclosure depicting application of force to the twisted hinge in a proximal direction to remove the hinge from housing portions of the tamper-resistant enclosure, and represents a stage of the illustrative method that is subsequent to that depicted in FIG. 2G.
Figure 2I:
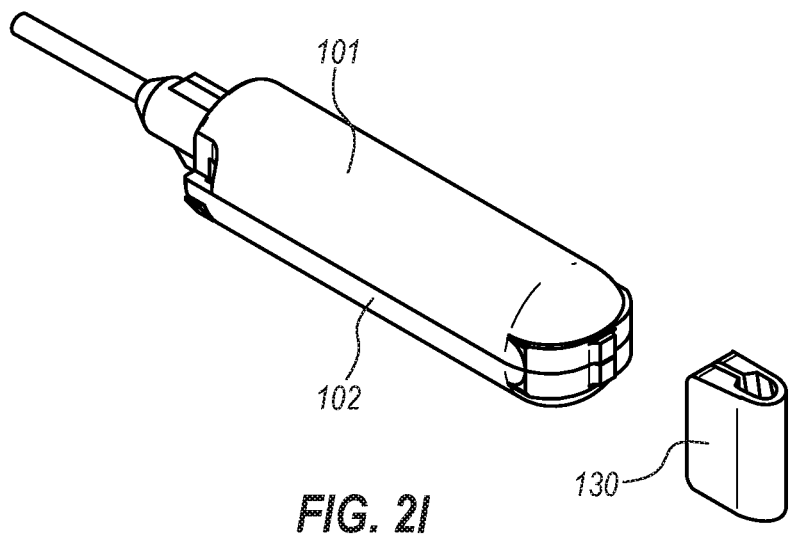
FIG. 2I is a perspective view of the tamper-resistant enclosure depicting the hinge having been removed from the housing portions of the tamper-resistant enclosure, and represents a stage of the illustrative method that is subsequent to that depicted in FIG. 2H.

FIG. 2H is a perspective view of the tamper-resistant enclosure 100 depicting application of force to the twisted hinge 130 in a proximal direction (the direction of the straight arrow) to remove the hinge 130 from housing portions 101, 102 of the tamper-resistant enclosure 100. FIG. 2I is a perspective view of the tamper-resistant enclosure 100 depicting the hinge 130 having been removed from the housing portions 101, 102 of the tamper-resistant enclosure 100. In this condition, the housing members 101, 102 can be readily separated from each other. For example, the locks at the opposite end of the enclosure 100 can be situated such that they provide little resistance to separation of the housing members 101, 102 when the hinged ends (or, rather, de-hinged ends) of the housing members 101, 102 are rotated away from each other or otherwise separated. Removal of the hinge 130 in manners such as just discussed may be referred to as activation of the tamper-evident indicator 111.

Figure 3A:
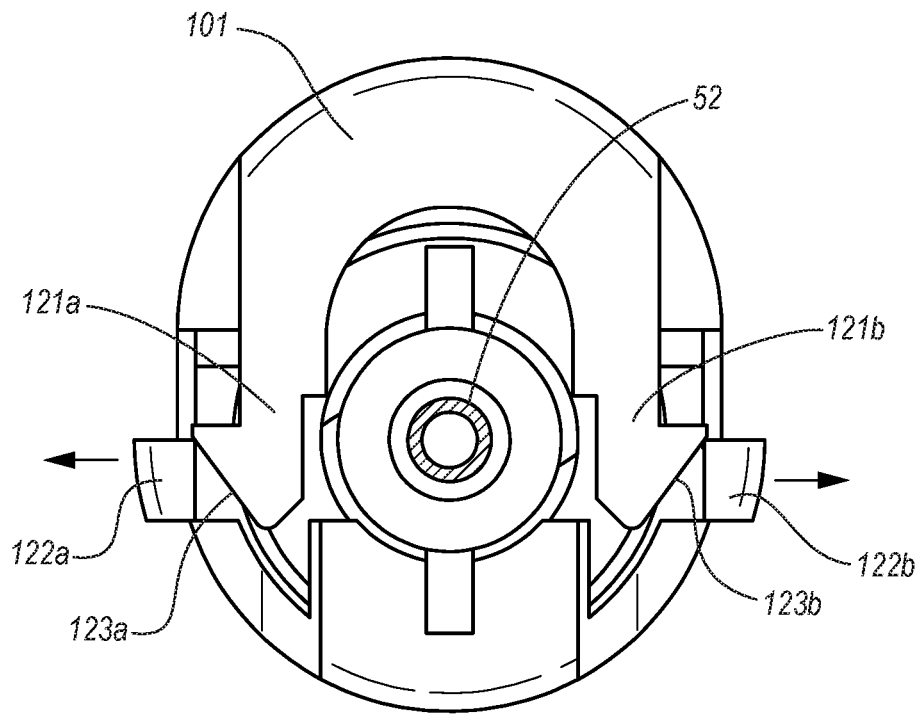
FIG. 3A is an end-on elevation view taken along a view line similar to the view line 3B-3B in FIG. 2D depicting the tamper-resistant enclosure transitioning from the open state to the closed state, and depicts a stage of an illustrative method of using the tamper-resistant enclosure that is between the stages depicted in FIGS. 2C and 2D.

FIG. 3A is an end-on elevation view taken along a view line similar to the view line 3B-3B in FIG. 2D depicting the tamper-resistant enclosure 100 transitioning from the open state to the closed state. Here, the camming surfaces 123a, 123b of the locking arms 121a, 121b urge the locking arms 122a, 122b laterally outward as the upper housing member 101 is urged downward.

Figure 3B:
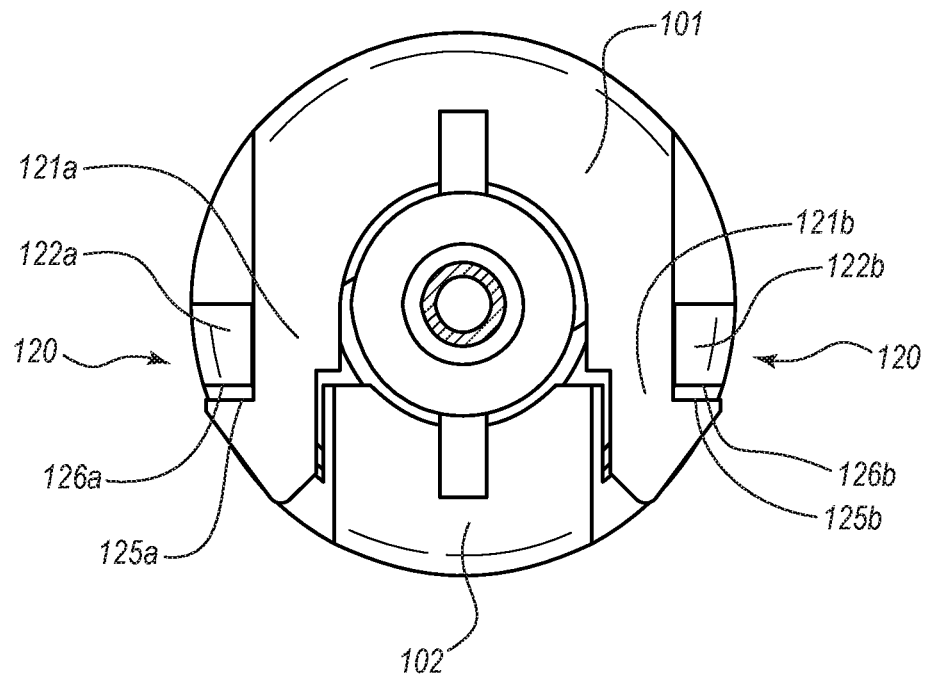
FIG. 3B is an end-on elevation view taken along the view line 3B-3B in FIG. 2D depicting the tamper-resistant enclosure in the closed state with a locking mechanism thereof in a locked state.

FIG. 3B is an end-on elevation view taken along the view line 3B-3B in FIG. 2D depicting the tamper-resistant enclosure 100 in the closed state with two locking mechanisms 120 thereof in a locked state. Opposing surfaces 125a, 126a and 125b, 126b of the locking arms 121a, 122a and 121b, 122b, respectively can abut and prevent separation of the first and second housing members 101, 102. The locking arms 122a, 122b can be resiliently flexible so as to automatically snap into the configuration shown in FIG. 3B. Stated otherwise, the locking arms 121a, 121b, 122a, 122b automatically engage each other when the housing members 101, 102 are moved into the closed state.

Whereas the locking mechanisms 120 in the illustrated embodiment are accessible when the housing members 101, 102 are in the closed state, in other embodiments, the locking mechanisms 120 are inaccessible. For example, the mechanisms may be internal to the housing members 101, 102 and thus not visible or accessible when the housing members 101, 102 are coupled. Such an arrangement may enhance the tamper resistance of the locking mechanisms 120.

In the illustrated embodiment, the locking mechanisms 120 are irreversible, such that one or more of the locking arms 121a, 121b, 122a, 122b must be deformed, broken, or otherwise altered to unlock the locking mechanism 120. For example, in various embodiments, the locking arms 121a, 121b may include a frangible region or may be plastically deformable about an axis that is perpendicular to the longitudinal axis of the closed device 100 (e.g., plastically deformable when rotated out of the page toward the reader) such that unlocking the mechanism 120 permanently deforms the locking arms 121a, 121b. In this manner, unlocking the locking mechanism 120 as just discussed may be referred to as activation of the tamper-evident indicator 110.

Figure 4A:
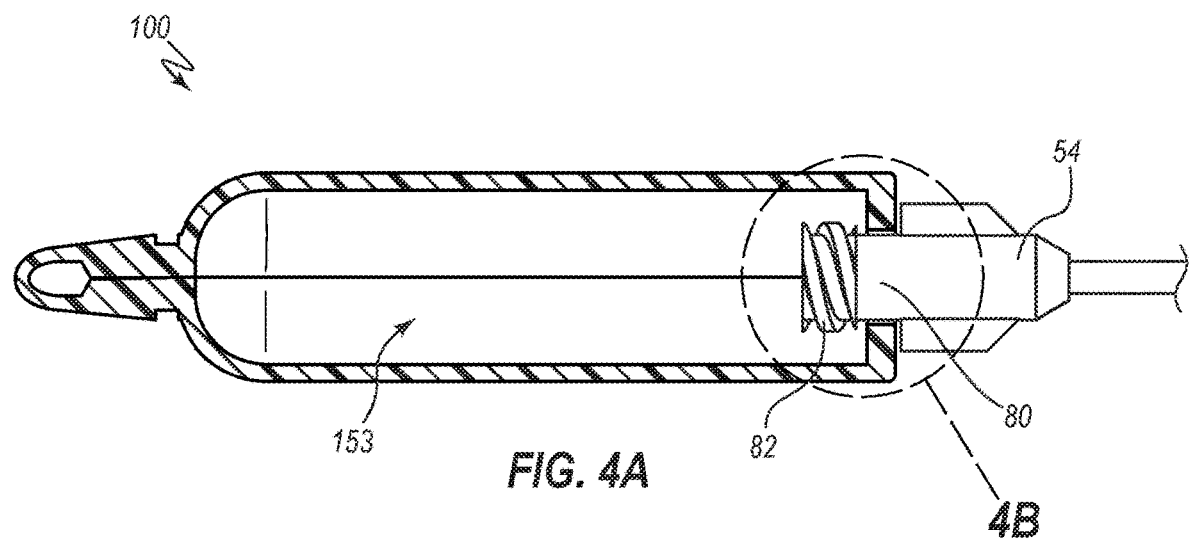
FIG. 4A is a cross-sectional view of the tamper-resistant enclosure in the closed state and encompassing a proximal portion of an embodiment of a medical connector at a proximal end of a medical fluid line.
Figure 4B:
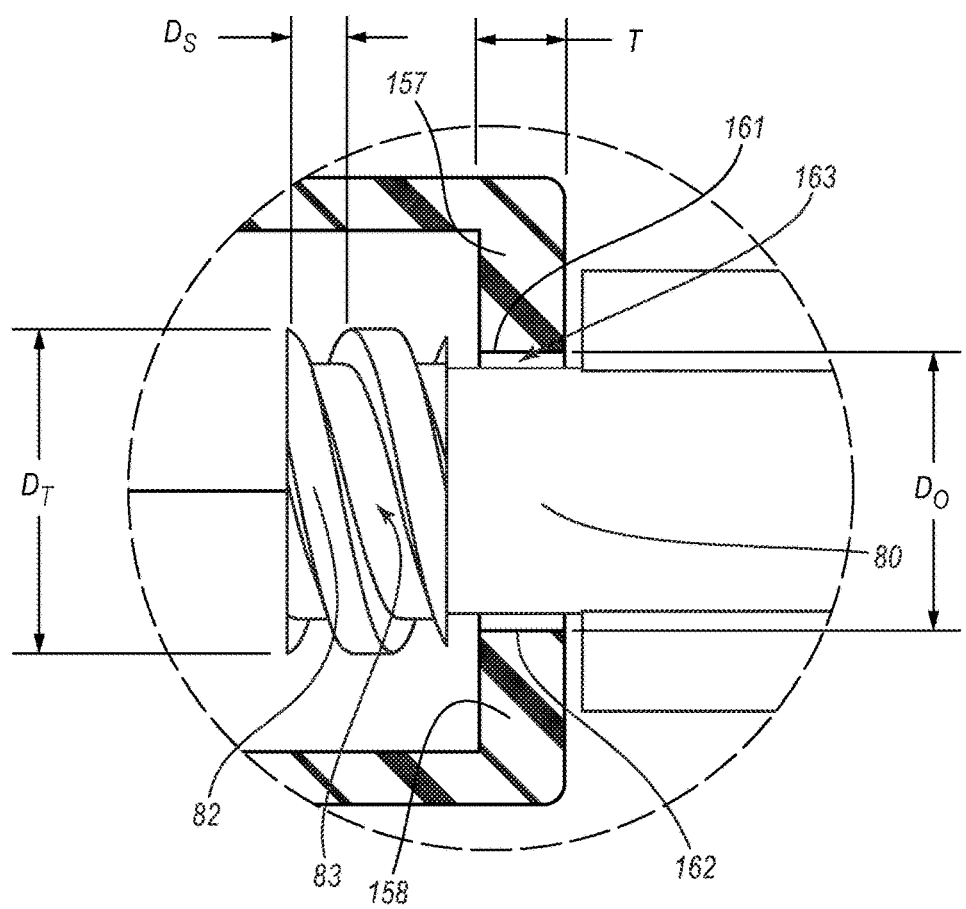
FIG. 4B is an enlarged view taken from the area identified by the view line 4B in FIG. 4A.

FIGS. 4A and 4B are cross-sectional views of the tamper-resistant enclosure 100 in the closed state and encompassing a proximal portion of an embodiment of the medical connector 54 at a proximal end of a medical fluid line. In this arrangement, the first and second stopping shelves 157, 158 encompass a neck portion 80 of the connector 54 and prevent a threaded region 82 from passing distally through the opening 163 defined by the opening surfaces 161, 162. In particular, the threading region 82 can define a maximum diameter $D_T$, which may also be referred to as a major diameter. The maximum diameter $D_T$ of the threading region 82 can exceed a maximum diameter $D_O$, which may also be referred to as a major diameter, of the opening 163. Accordingly, the first and second stopping shelves 157, 158 can constrict the threading region 82 of the connector 54 and prevent it from being retracted out of the enclosure 100.

In some embodiments, it can be desirable to ensure that the threading or threaded region 82 of the connector 54 may not be manipulated or rotated against the base end of the housing to extract the connector 54 from the housing. To this end, a thickness T of a base portion of the housing, which is defined by the first and second stopping shelves 157, 158 in the present embodiment, is greater than a separation distance $D_S$ between adjacent threading portions of the threaded region 82. In some embodiments, it may be sufficient for just one of the shelves 157, 158 to be thicker than the separation distance $D_S$. In other embodiments, such as that illustrated, both stopping shelves 157, 158 may be thicker than the separation distance $D_S$.

FIG. 5 is a cross-sectional view of another embodiment of a tamper-resistant enclosure 200 in a closed state. The tamper-resistant enclosure 200 resembles the tamper-resistant enclosure 100 described above in certain respects. Accordingly, like features are designated with like reference numerals, with the leading digits incremented to "2." Relevant disclosure set forth above regarding similarly identified features thus may not be repeated hereafter. Moreover, specific features of the enclosure 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the enclosure 200 and related components depicted in FIG. 5. Any suitable combination of the features, and variations of the same, described with respect to the enclosure 100 can be employed with the enclosure 200, and vice versa. This pattern of disclosure applies equally to further embodiments depicted in subsequent figures and described hereafter, wherein the leading digits may be further incremented.

The enclosure 200 encompasses a proximal portion of an embodiment of the medical connector 54 at a proximal end of a medical fluid line. In this arrangement, first and second stopping shelves 257, 258 encompass a catheter portion 52 of the fluid line 50. The stopping shelves 257, 258 define a smaller opening 263 than the opening 163 described above, and are configured to prevent any of the connector 54 from passing distally through the opening 263. In particular, a distal end of the medical connector 54 can define a maximum diameter, which may also be referred to as a major diameter. The maximum diameter of the distal end of the medical connector 54 can exceed a maximum diameter, which may also be referred to as a major diameter, of the opening 263. Accordingly, the first and second stopping shelves 257, 258 can constrict the distal end of the medical connector 54 and prevent it from being retracted out of the enclosure 200.

FIGS. 6-18B depict embodiments of a tamper-resistant enclosure configured for use with a catheter system that has two luer ends. The device includes two cavities for receiving two separate luer ends. FIGS. 19-27 depict another embodiment that has a single cavity that can be used with a single luer end. Any other suitable number of cavities is contemplated.

The tamper-resistant enclosures can receive the luer ends and/or sterility caps that are coupled thereto and prevent tampering. As previously mentioned, the enclosures can define an opening through which a portion of a luer or other suitable catheter communication device can extend, and the cavity of the housing can be sufficiently large to receive the proximal end of the luer or other device and/or a cap coupled thereto. When the enclosure is closed and locked, the proximal end and/or cap are retained securely inside and cannot be removed without breaking the locking mechanism. This can inhibit and/or prevent tampering. This can also provide a tamper-evident feature.

In the illustrated embodiments below, the locking is provided by a zip tie. In other or further embodiments, a tamper-evident sticker is applied from one side of the enclosure to the other. Any other suitable locking mechanism and/or tamper-evident mechanism is contemplated.

Figure 6:
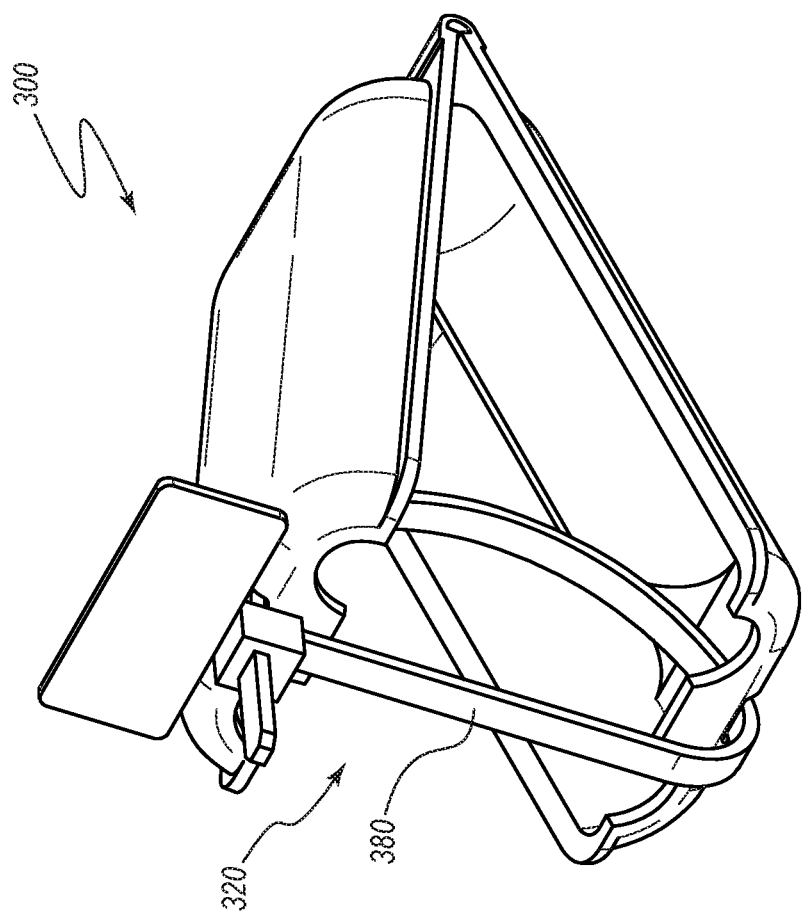
FIG. 6 is a perspective view of another embodiment of a tamper-resistant enclosure in an open state.

FIG. 6 is a perspective view of an embodiment of another embodiment of a tamper-resistant enclosure 300 in an open state. The enclosure 300 includes a locking mechanism 320. In particular, the locking mechanism 320 is a fastener of any suitable variety. In the illustrated embodiment, the fastener is a zip tie 380.

Figure 7:
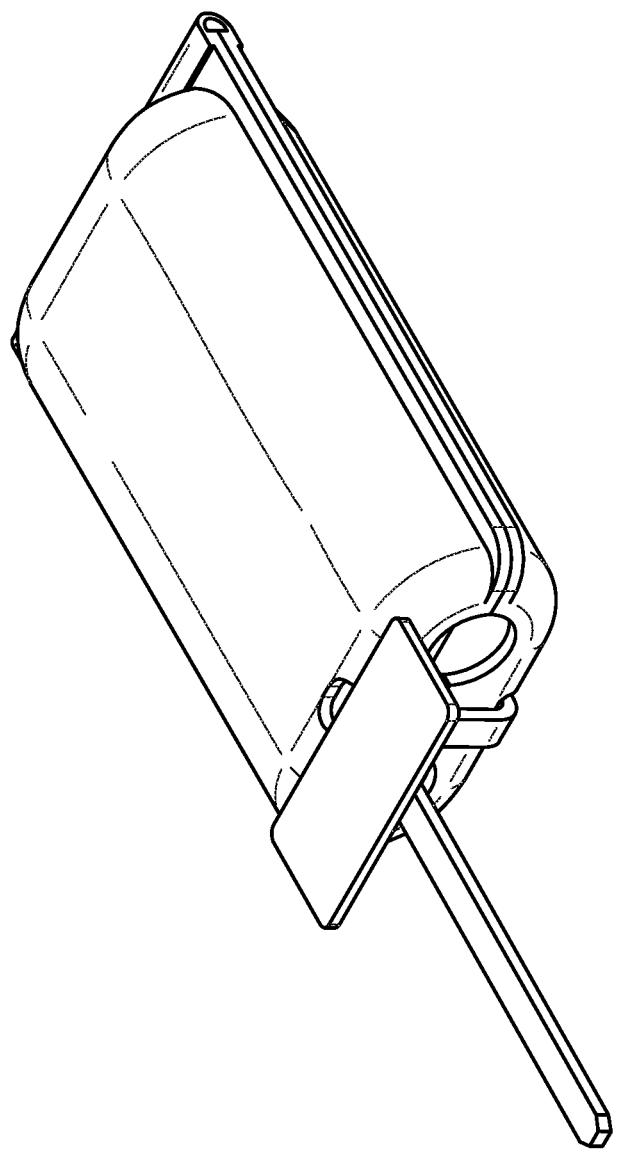
FIG. 7 is a perspective view of the tamper-resistant enclosure of FIG. 6 in a closed state, and further, in a locked state.

FIG. 7 is a perspective view of the tamper-resistant enclosure 300 in a closed state, and further, in a locked state. In particular, the zip tie 380 has been cinched to a tightly locked condition.

Figure 8:
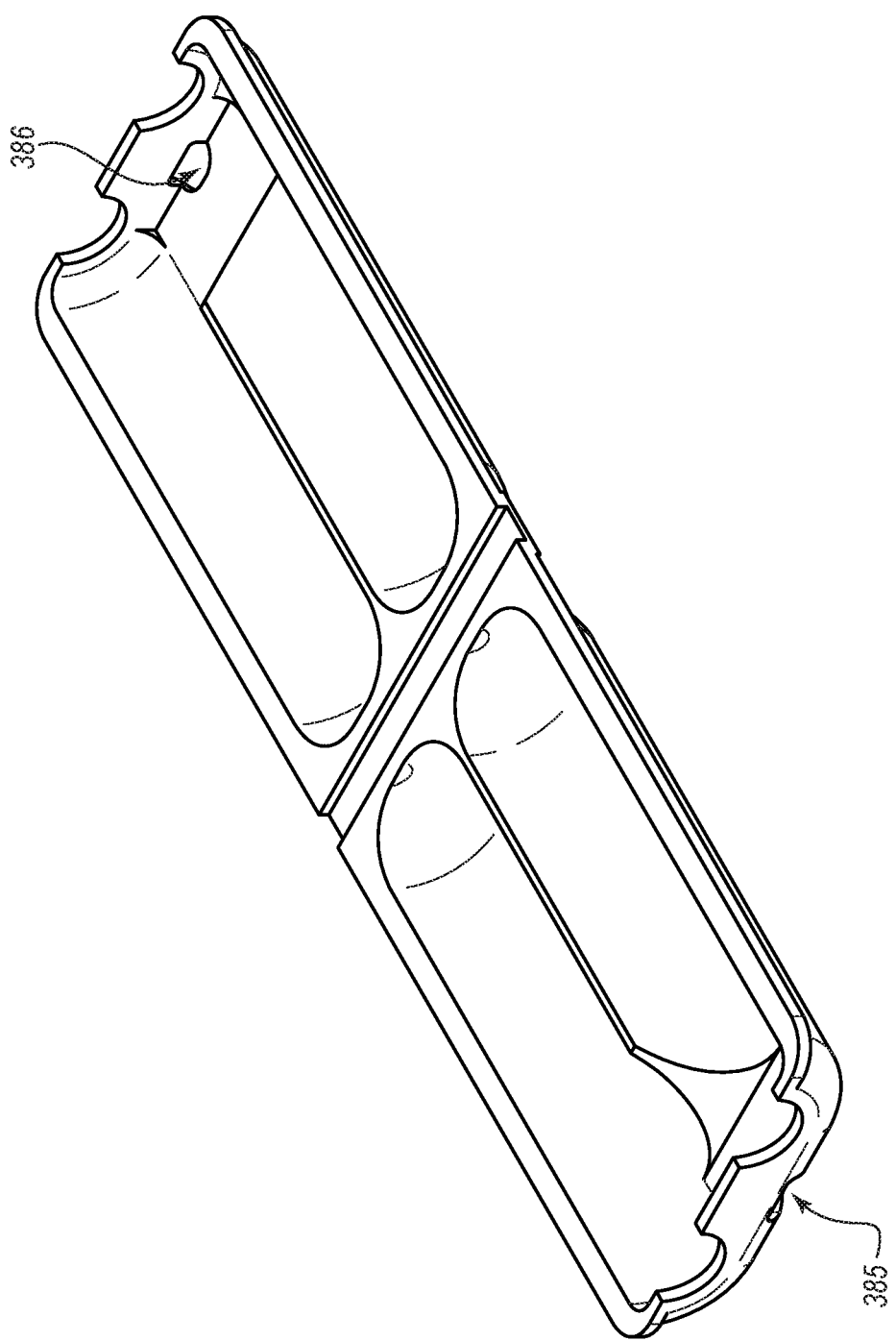
FIG. 8 is a perspective view of a housing portion of the tamper-resistant enclosure of FIG. 6 in a fully open configuration, wherein the interior of the housing is depicted.

FIG. 8 is a perspective view of a housing portion of the tamper-resistant enclosure of FIG. 6 in a fully open configuration, wherein the interior of the housing is depicted. Two housing members each define an opening 385, 386 through which the fastener 380 extends to lock the housing when in a closed state.

Figure 9:
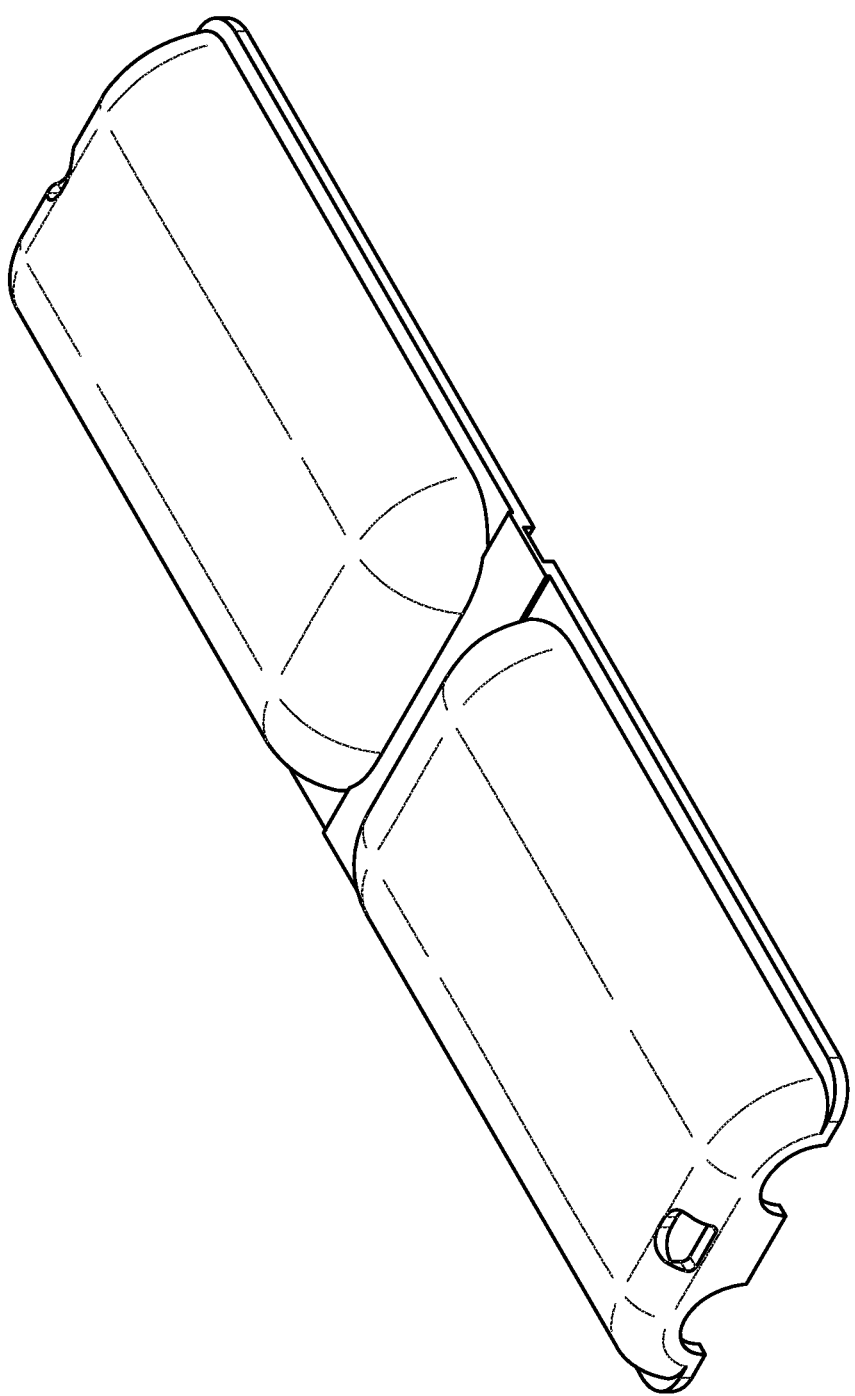
FIG. 9 is another perspective view of the housing portion of FIG. 8 in the fully open configuration, wherein the exterior of the housing is depicted.
Figure 10:
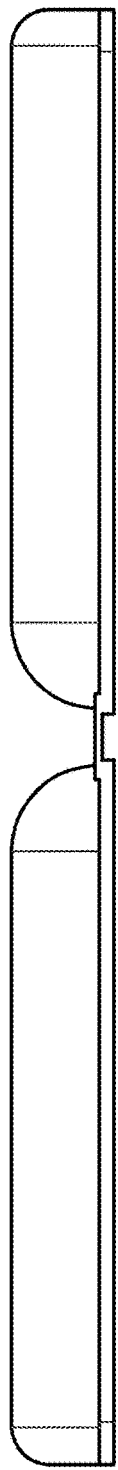
FIG. 10 is a side elevation view of the housing.
Figure 11:
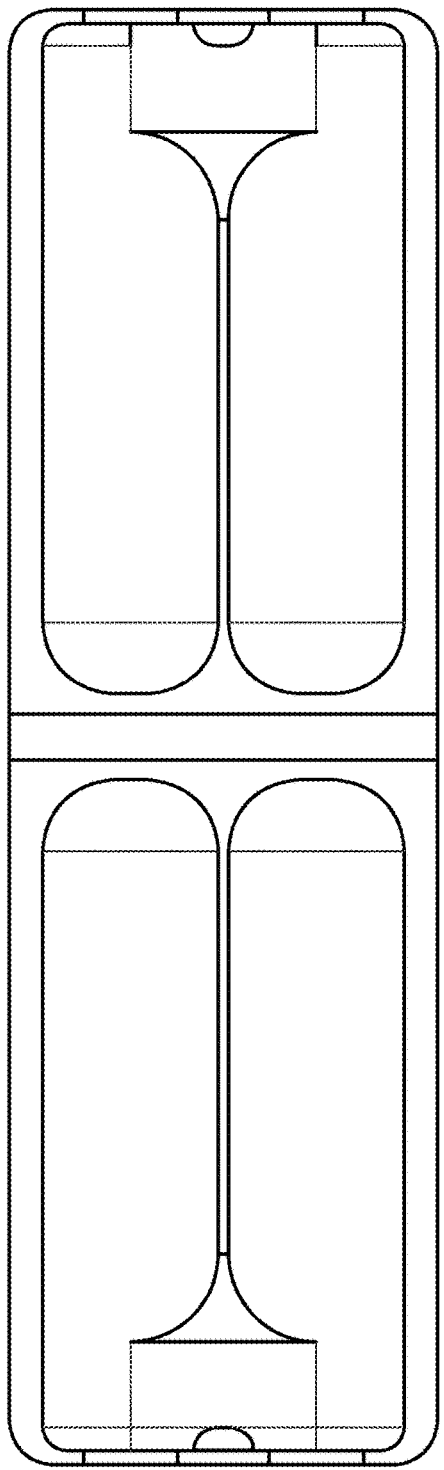
FIG. 11 is a top plan view of the housing showing the interior.
Figure 12:
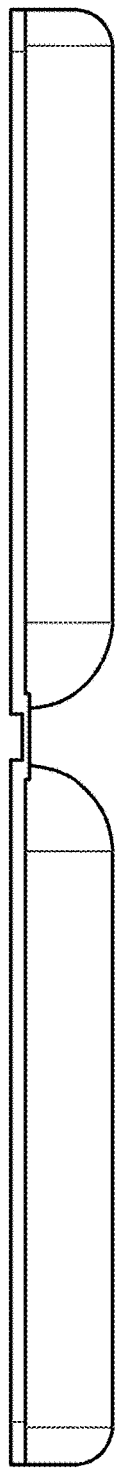
FIG. 12 is an opposite side elevation view of the housing.

FIG. 9 is another perspective view of the housing portion of FIG. 8 in the fully open configuration, wherein the exterior of the housing is depicted. FIG. 10 is a side elevation view of the housing. FIG. 11 is a top plan view of the housing showing the interior. FIG. 12 is an opposite side elevation view of the housing. FIG. 13 is a bottom plan view of the housing showing the exterior. FIG. 14 is an end elevation view of the housing. FIG. 15 is an opposite end elevation view of the housing.

Figure 16:
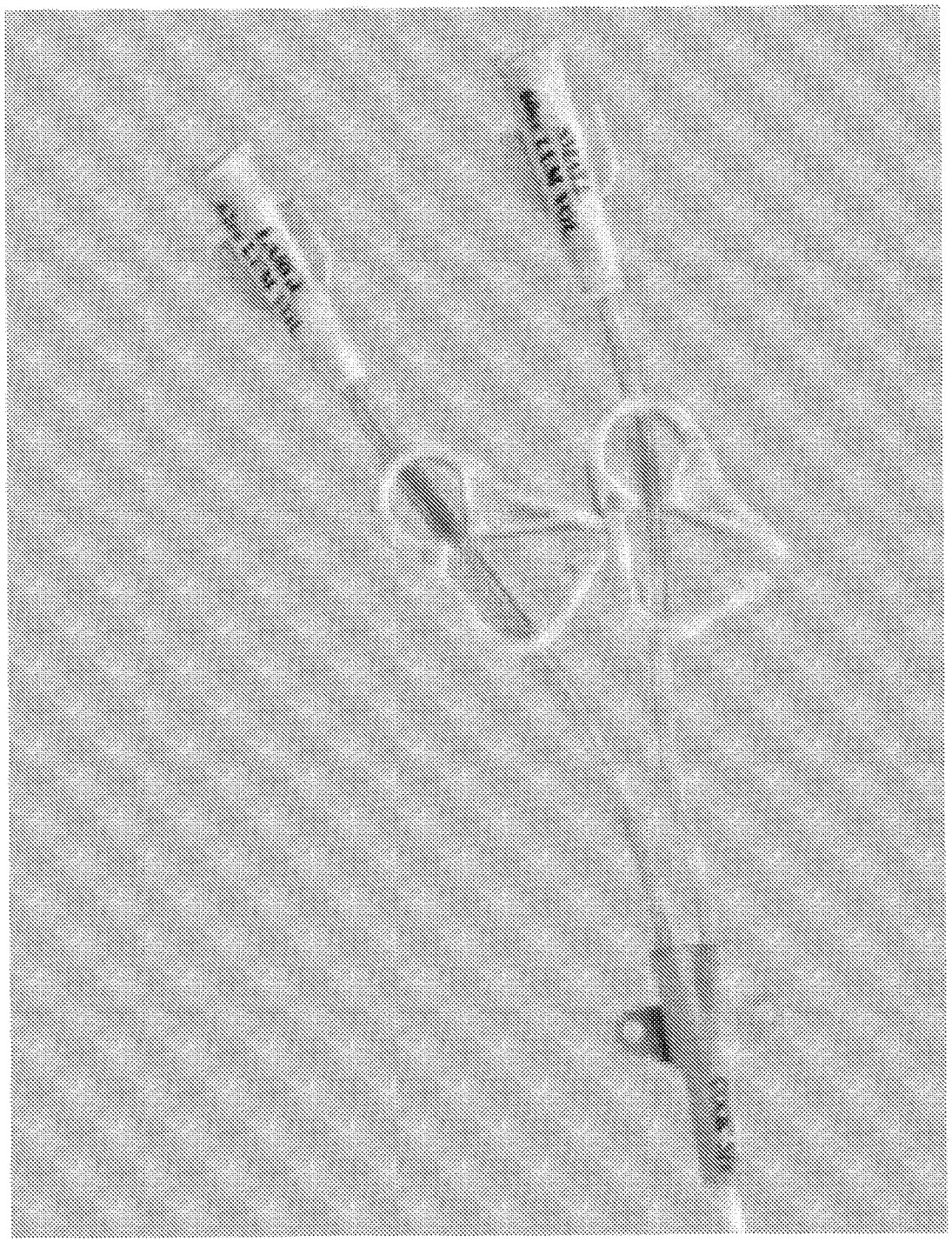
FIG. 16 is an image of an embodiment of a catheter system with which the enclosure of FIG. 6 or the enclosure of FIG. 1 is compatible.
Figure 17:
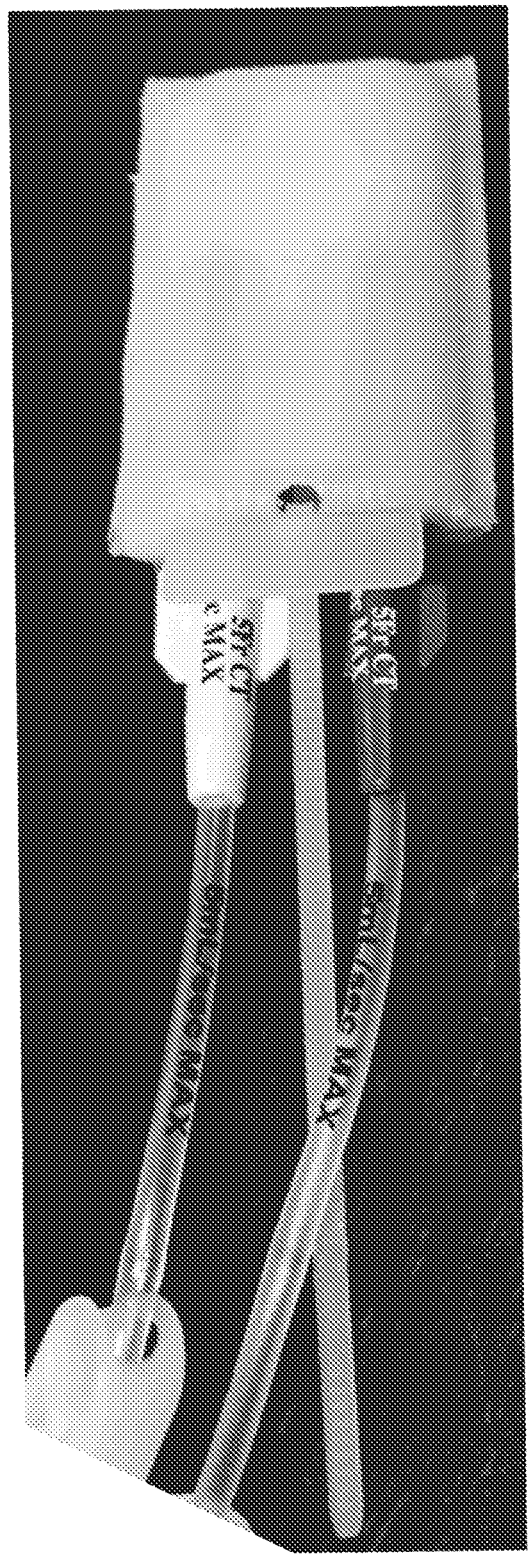
FIG. 17 is an image of the tamper-resistant enclosure of FIG. 6 in use with the catheter system of FIG. 16, wherein luers at the end of the catheter of FIG. 16 are fitted with sterility caps (such as the cap depicted in FIG. 19), and proximal ends of the luers and the caps that are engaged therewith are received within the tamper-resistant enclosure, and further, the tamper-resistant enclosure is in a closed and locked state to prevent undesired tampering with the enclosed luers.

FIG. 16 is an image of an embodiment of a catheter system with which the enclosure of FIG. 6 is compatible. FIG. 17 is an image of the tamper-resistant enclosure of FIG. 6 in use with the catheter system of FIG. 16, wherein luers at the end of the catheter of FIG. 16 are fitted with sterility or disinfectant caps (such as the cap depicted in FIG. 19), and proximal ends of the luers and the caps that are engaged therewith are received within the tamper-resistant enclosure, and further, the tamper-resistant enclosure is in a closed and locked state to prevent undesired tampering with the enclosed luers.

Figure 18A:
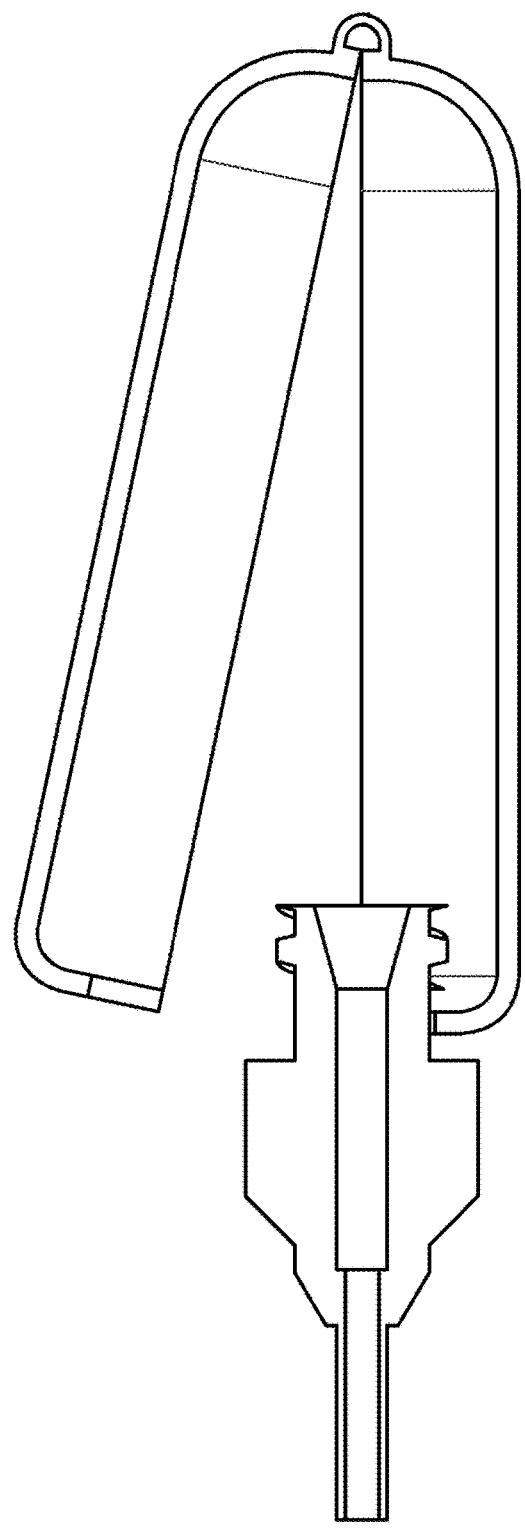
FIG. 18A is a cross-sectional view of the housing in the open state with the proximal end of the luer positioned at an interior of the housing with a neck of the luer positioned at an opening in the housing.
Figure 18B:
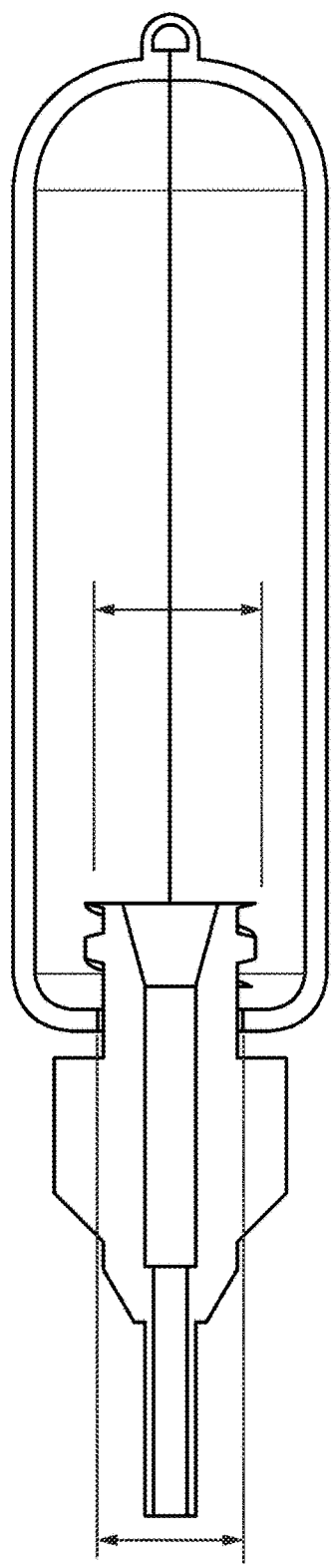
FIG. 18B is another cross-sectional view of the housing, where the housing has been transitioned to the closed state, FIG. 13B demonstrating that the neck of the luer fits within the opening defined by the housing (whether snugly or loosely), and the threaded proximal end of the luer is incapable of passing through the opening defined by the housing.
Figure 19:
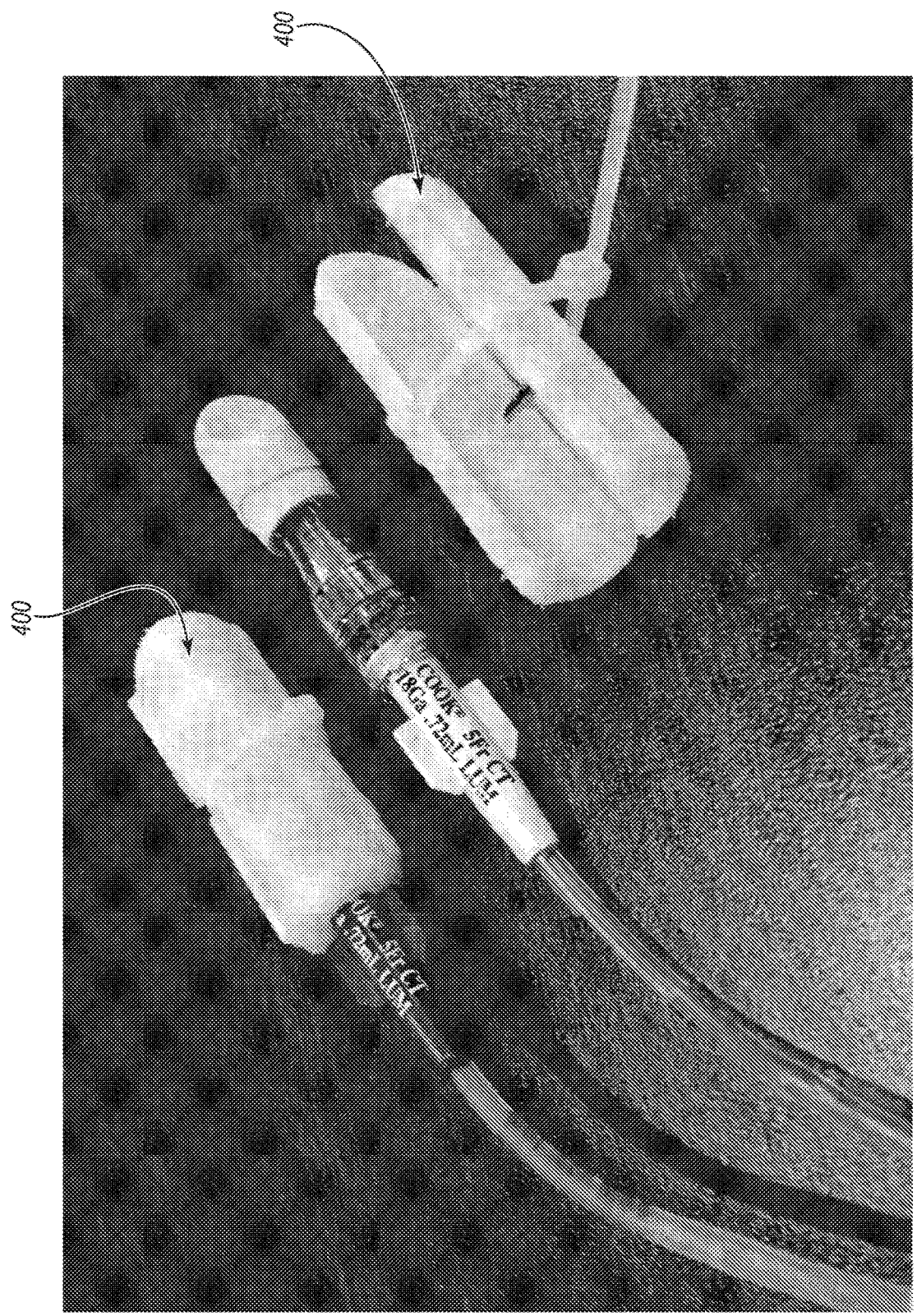
FIG. 19 is an image of two samples of another embodiment of a tamper-resistant enclosure, with one sample shown in a closed and locked state and the other sample (in the foreground) shown in an open and unlocked state.
Figure 20:
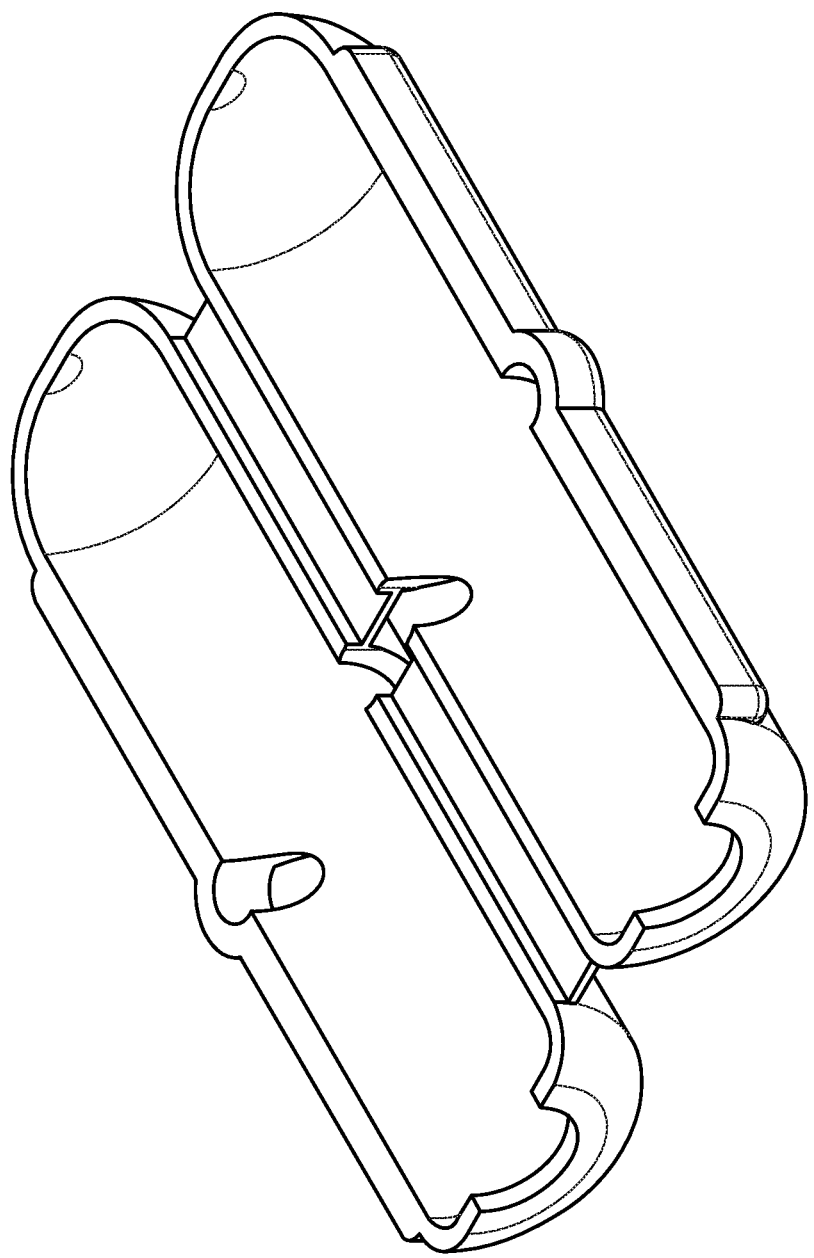
FIGS. 20-27 are various views of a housing portion of the tamper-resistant enclosure of FIG. 19, which depict perspectives of the housing portion such as those described relative to FIGS. 8-15, respectively.
Figure 21:
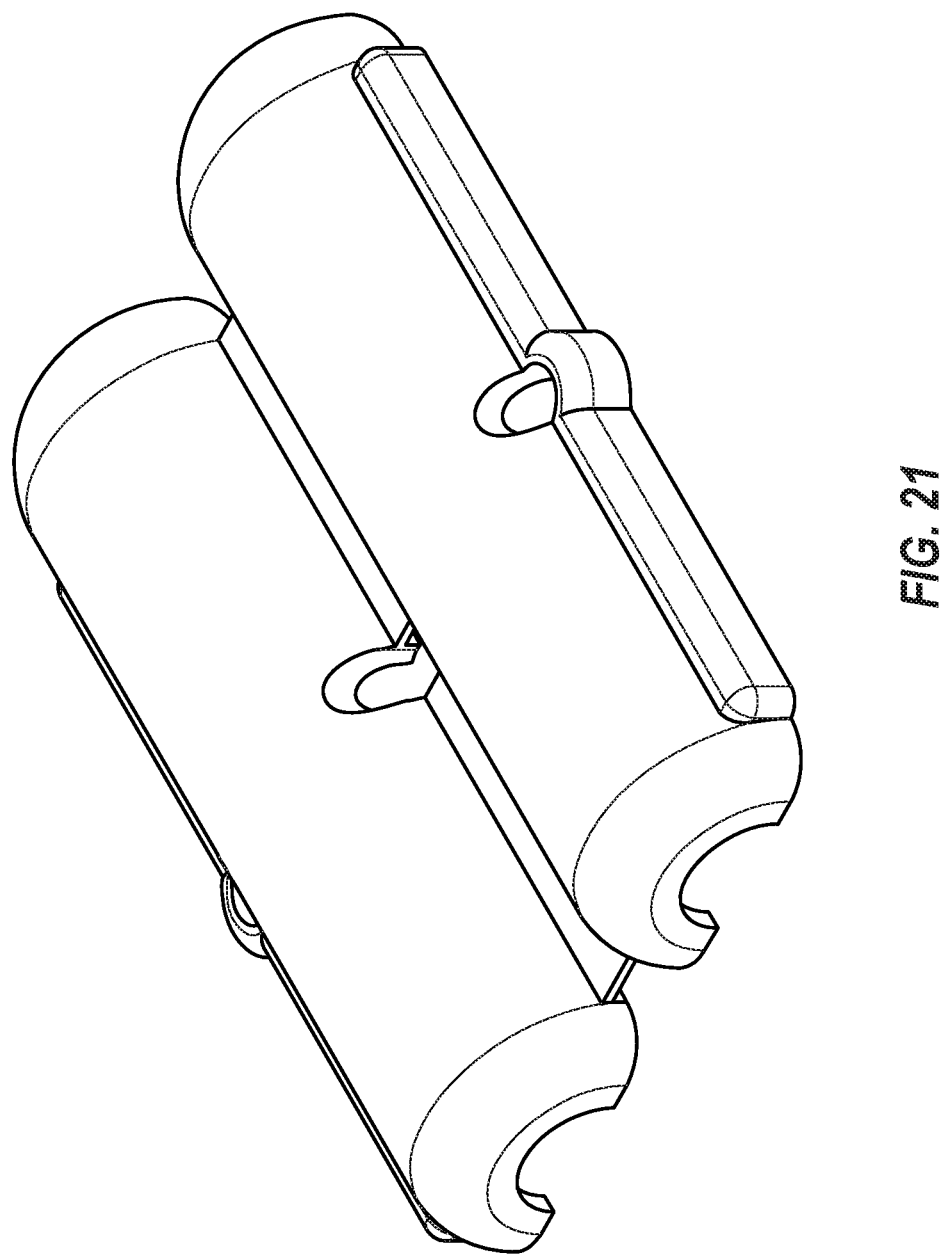
Figure 22:
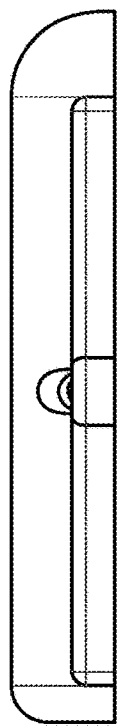
Figure 23:
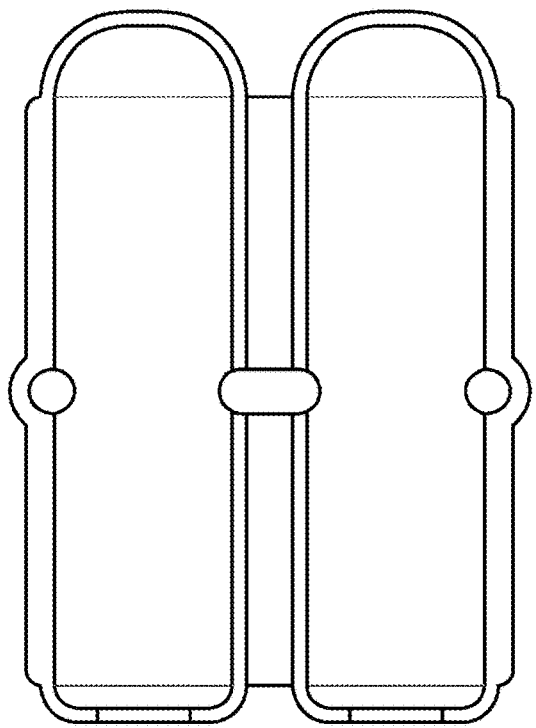
Figure 24:
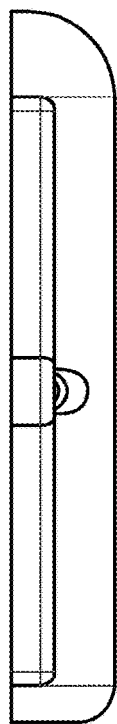
Figure 25:
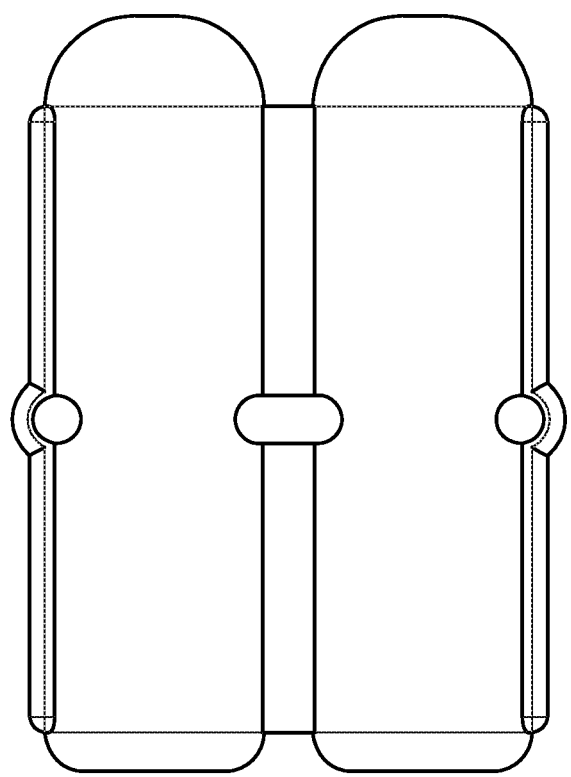
Figure 27:
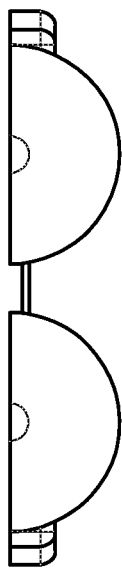
Figure 26:
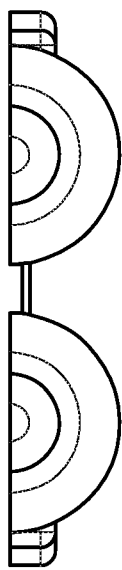

FIG. 18A is a cross-sectional view of the housing in the open state with the proximal end of the luer positioned at an interior of the housing with a neck of the luer positioned at an opening in the housing. FIG. 18B is another cross-sectional view of the housing, where the housing has been transitioned to the closed state, FIG. 13B demonstrating that the neck of the luer fits within the opening defined by the housing (whether snugly or loosely), and the threaded proximal end of the luer is incapable of passing through the opening defined by the housing;

FIG. 19 is an image of two samples of another embodiment of a tamper-resistant enclosure 400, with one sample shown in a closed and locked state and the other sample (in the foreground) shown in an open and unlocked state.

FIGS. 20-27 are various views of a housing portion of the tamper-resistant enclosure of FIG. 19, which depict perspectives of the housing portion such as those described relative to FIGS. 8-15, respectively.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Any reference throughout this specification to "certain embodiments" or the like means that a particular feature, structure or characteristic described in connection with that embodiment is included in at least one embodiment. Thus, the quoted phrases, or variations thereof, as recited throughout this specification are not necessarily all referring to the same embodiment or embodiments.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Embodiments of the invention in which an exclusive property or privilege is claimed are defined as follows.

The invention claimed is:

1. A tamper-resistant device for holding at least a first portion of an access port of a medical fluid line, the first portion of the access port comprising a threaded region that defines a first major diameter, and a distal end of the access port defining a second major diameter smaller than the first major diameter, the device comprising:
   a first housing member comprising a first recess and a first stopping shelf;
   a second housing member comprising a second recess and a second stopping shelf, the second housing member being configured to couple with the first housing member such that the first and second recesses cooperate to define a cavity sized to receive the first portion of the access port of the fluid line, such that the first and second stopping shelves cooperate to retain at least the first portion of the access port within the cavity;
   a locking mechanism configured to maintain the first and second housing members in a coupled state when the locking mechanism is engaged; and
   a tamper-evident indicator that, when activated, permits the first and second housing members to transition from the coupled state to a decoupled state to permit access to the first portion of the access port of the fluid line, wherein the tamper-evident indicator comprises a hinge coupled to each of the first and second housing members, wherein the hinge is configured to be removed from each of the first and second housing members by axial rotation of the hinge relative to the first and second housing members.

2. The tamper-resistant device of claim 1, wherein the hinge is positioned opposite each of the first and second shelves.

3. The tamper-resistant device of claim 1, wherein the first housing member, the second housing member, and the hinge are integrally formed of a unitary piece of material.

4. The tamper-resistant device of claim 1, wherein removal of the hinge from the first and second housing members permits the first and second housing members to transition from the coupled state to the decoupled state.

5. The tamper-resistant device of claim 1, wherein the hinge is coupled to the first housing member via a first breakaway mechanism and is coupled to the second housing member via a second breakaway mechanism.

6. The tamper-resistant device of claim 1, wherein the hinge is coupled to the first housing member via a first frangible connection and is coupled to the second housing member via a second frangible connection.

7. The tamper-resistant device of claim 1, wherein the hinge comprises a living hinge.

8. The tamper-resistant device of claim 1, wherein the locking mechanism comprises a second tamper-evident indicator.

9. The tamper-resistant device of claim 1, wherein the locking mechanism is configured to engage automatically when the first and second housing members are transitioned to the coupled state.

10. The tamper-resistant device of claim 1, wherein the locking mechanism is configured to be inaccessible once engaged to prevent disengagement of the locking mechanism.

11. The tamper-resistant device of claim 1, further comprising a sticker configured to contact both of the first and second housing members when the first and second housing members are in the coupled state, wherein activation of the sticker comprises removing at least a portion of the sticker from the first and second housing members.

12. The tamper-resistant device of claim 1, wherein the first housing member comprises a first closed end opposite the first stopping shelf and the second housing member comprises a second closed end opposite the second stopping shelf.

13. The tamper-resistant device of claim 1, wherein each of the first and second housing members defines a separate opening through which the locking mechanism extends.

14. The tamper-resistant device of claim 1, wherein the threaded region comprises threads that define a separation distance between adjacent threading portions, and wherein at least one of the first and second stopping shelves defines a thickness that is larger than the separation distance.

15. A tamper-resistant device for holding an access portion of a medical fluid line, the device comprising:
   a first housing member comprising a first recess;
   a second housing member comprising a second recess, the second housing member being configured to couple with the first housing member such that the first and second recesses cooperate to define a cavity sized to receive the access portion of the fluid line;
   a locking mechanism configured to maintain the first and second housing members in a coupled state when the locking mechanism is engaged; and
   a hinge coupled to the first housing member via a first breakaway mechanism and coupled to the second housing member via a second breakaway mechanism,
   wherein when the first and second housing members are in the coupled state and the locking mechanism is engaged, removal of the hinge from the first and second housing members via axial rotation of the hinge at the first and second breakaway mechanisms permits the first and second housing members to be transitioned from the coupled state to a decoupled state to permit access to the access portion of the fluid line.

16. The tamper-resistant device of claim 15, wherein the first housing member, the second housing member, and the hinge are integrally formed of a unitary piece of material.

* * * * *